United States Patent [19]
Wickramasinghe et al.

[11] Patent Number: 5,538,898
[45] Date of Patent: Jul. 23, 1996

[54] METHOD SUITABLE FOR IDENTIFYING A CODE SEQUENCE OF A BIOMOLECULE

[75] Inventors: Hemantha K. Wickramasinghe, Chappaqua; Frederic Zenhausern, Mohegan Lake, both of N.Y.

[73] Assignee: International Business Machines Corporation, Armonk, N.Y.

[21] Appl. No.: 405,070

[22] Filed: Mar. 16, 1995

[51] Int. Cl.$^6$ ............................................. G01N 33/48
[52] U.S. Cl. ............................ 436/94; 436/164; 436/177; 422/82.01; 422/82.05; 422/82.08; 422/82.12
[58] Field of Search ............................ 436/94, 164, 177, 436/156; 422/50, 63, 65, 82.01, 82.05, 82.08, 82.12

[56] References Cited

U.S. PATENT DOCUMENTS

| | | | |
|---|---|---|---|
| 4,343,993 | 8/1982 | Binnig et al. | 250/306 |
| 4,747,698 | 5/1988 | Wickramasinghe et al. | 374/6 |
| 4,917,462 | 4/1990 | Lewis et al. | 350/319 |
| 4,941,753 | 7/1990 | Wickramasinghe | 374/120 |
| 4,947,034 | 8/1990 | Wickramasinghe et al. | 250/216 |
| 5,003,815 | 4/1991 | Martin et al. | 73/105 |
| 5,272,330 | 12/1993 | Betzig et al. | 250/216 |
| 5,319,977 | 6/1994 | Quate et al. | 73/606 |
| 5,362,653 | 11/1994 | Carr et al. | 436/165 |
| 5,479,024 | 12/1995 | Hillner et al. | 250/458.1 |
| 5,485,536 | 1/1996 | Islam | 385/31 |

OTHER PUBLICATIONS

C. R. Cantor et al, Pulsed–Field gel electrophoresis of very large–DNA molecules, Annual Review of Biophysics and Biophysical Chemistry, vol. 17,287,1988.
Y. F. Chen et al, Anal. Chem., 62, 496–503, 1990.
Mayer et al (Anal. Chem. 1994, 66, 1777–1780).
R. Drmanac et al, "Sequencing of Magabase Plus DNA by Hybridization: Theory of the Method" in Genomics, vol. 4, pp. 114–118 (1989), respectively Appl. Phys. Lett 65(13), 26 Sep. 1994.
V. Lund et al, Nucleic Acid Res., 16(22), 10861–80, 1988.

Primary Examiner—Lyle A. Alexander
Attorney, Agent, or Firm—Stephen C. Kaufman

[57] ABSTRACT

A method suitable for identifying a code sequence of a biomolecule. The method comprises the steps of using a near-field probe technique for generating a super-resolution chemical analysis of at least a portion of the biomolecule; and, correlating the chemical analysis with a broad spectral content of a referent biomolecule for generating code sequencing.

43 Claims, 13 Drawing Sheets

METHOD SUITABLE FOR IDENTIFYING A CODE SEQUENCE OF A BIOMOLECULE

This application is related to application Ser. No. 08/405,476 filed Mar. 16, 1995 by H. K. Wickramasinghe and F. Zenhausern (YO995-058) and to application Ser. No. 08/405,481 filed Mar. 16, 1995 by F. Zenhausern and H. K. Wickramasinghe (YO995-061)and to application Ser. No. 08/405,068 filed Mar. 16, 1995 by F. Zenhausern and H. K. Wickramasinghe (YO995-065), which applications are being filed contemporaneously with this application. The entire disclosures of those applications, all of which are copending and commonly assigned, are incorporated by reference herein.

FIELD OF THE INVENTION

This invention relates to a method suitable for identifying a code sequence of at least a portion of a biomolecule.

BACKGROUND OF THE INVENTION

Four classes of biological molecules are known, namely, those comprising proteins, lipids, carbohydrates and nucleic acids. Nucleic acids, in turn, comprise two subsumed classes: DNA which is a genetic component of all cells, and RNA which usually functions in a synthesis of proteins.

The purview of the present invention extends to biomolecules, generally, but a working point for the sake of pedagogy is now established by referencing biomolecules comprising DNA. DNA is emphasized because it is the prime genetic molecule, carrying all hereditary information within chromosomes.

DNA stands for deoxyribonucleic acid. The DNA of most cells resides in a cell's nucleus. Its structure comprises long chains of relatively simple molecules called nucleotides. Each nucleotide comprises three parts: (1) a phosphate group stripped of one special oxygen atom; (2) a sugar called "ribose"; and (3) a base. It is the base alone which distinguishes one nucleotide from another—thus it suffices to specify a base to identify a nucleotide. The four types of bases which occur in DNA nucleotides are adenine (A); guanine (G), cytosine (C) and thymine (T).

A single strand of DNA comprises many nucleotides strung together like a chain of beads. DNA usually comes in double strands, that is, two single strands which are paired up, nucleotide by nucleotide, in the form of the well known DNA double helix.

DNA carries a vast array of information through its nucleotide sequence. Accordingly, the order of nucleotides (considered as a linear progression e.g., "A T T C G G A C C . . . ") is highly varied. A nucleotide sequence may comprise inter alia a single nucleotide, a duplet (adjacent pairs of bases), a codon (three consecutive bases), a gene (a portion of a strand which codes liar a single enzyme), a strand of arbitrary nucleotides, or a genome comprising a total set of DNA molecules for an organism (e.g., $3 \times 10^9$ nucleotides for a human cell).

SUMMARY OF THE INVENTION

Our work relates to a novel approach and method for biomolecular code sequencing. We proceed from the following considerations.

First, we set forth why it is significant and of great utility to have a biomolecular code sequencing capability. This effort, secondly, can help elicit problems, difficulties and constraints in an attempt to realize and effect such a capability. Thirdly, we situate what is of pertinence with respect to the prior art as it relates to this situation. Finally, we define the novel method of the present invention, and argue that it addresses and solves the problems to be overcome in realizing a qualitatively new method comprising biomolecular code sequencing. Furthermore, we set the novel method in a position to the prior art, thereby highlighting its novel and unobvious aspects as well as attesting to its advantages.

Accordingly, we assume firstly that one somehow has nucleotide sequencing information, and that this information may be accessed by conventional computer techniques. Then, once in the computer, nucleotide sequences can be scanned (at least theoretically, in some cases) inter alia for RNA synthesis, a presence of inverted palindromes, preferred segments of potential Z—DNA (alternating purine and pyrimidine stretches), homologies to other known DNA sequences, mutation detection, genotyping, genetic database comparing, or large-scale supersequencing specifying a human genome by way or its component nucleotides and their location with respect to the entire genome.

It is believed that this recital makes self-evident the significance and utility of a biomolecular code sequencing capability. At the same time, it provokes outstanding difficulties, problems and constraints implicit in an hypothesized method for effecting such a sequencing capability. For example, a genome comprises approximately $10^9$ nucleotides and has an average length of approximately 0.6 m, and a single nucleotide has an average length of approximately 1 to two angstroms. A candidate methodology must at least, therefore, somehow be able to resolve one nucleotide from an adjacent nucleotide, presumably without damage to the nucleotide, and resolve significant numbers of such nucleotides with precision and accuracy and within a meaningful time span.

Two important and representative prior art methodologies that are pertinent to this situation comprise separation techniques including gel electrophoresis and free-solution electrophoresis.

Gel electrophoresis requires a physical separation of DNA fragments produced during a sequencing reaction. Instruction on conventional gel electrophoresis may be found in (1) J. Sambrook, E. F. Fritsch, T. Maniantis, "Molecular Cloning: A Laboratory Manual" (Cold Spring Harbor Laboratory, N.Y. 1989), (2) A. T. Bankier and B. G. Barrel, "Nucleic Acids Sequencing: A Practical Approach", Eds. E. M. Howe, C. I. Rowlings, IRL Press, Oxford 1989, pp. 37–73, which instruction is incorporated by reference herein.

In overview, gel electrophoresis methodology typically comprises the steps of: (1) fragmenting a DNA strand to be sequenced into a series starting from the same point on the strand, each figment different in length to the other by one nucleotide; (2) labelling each fragment with e.g., fluorescent tags which can fluoresce at different colours depending on the end base (A,T, C or G); (3) doing gel electrophoresis for sequentially separating the fragments into bands of decreasing molecular size; and (4) using a suitable detection means for determining the end label of each band.

To this end, present gel electrophoresis methodology relics on a dispersion in the mobility of the DNA molecules with length to separate and effect bands in an electric field. Gel electrophoresis methodology, as it is presently understood, accordingly, is therefore disadvantageously limited to approximately 700 bases (nucleotides) because there is a saturation in the dispersion for molecular lengths longer than 700 nucleotides. Further, due to the low dispersion and mobility, it takes several hours to achieve the separation of 700 nucleotides. It is true that this speed can be marginally increased by having several lanes/up to say 36 sequencing different portions of a strand.

An important advantage of the present invention is that, notwithstanding the present difficulties or deficiencies of gel electrophoresis, as just noted, it is able to offset or remedy these limitations, so that as modified or re-evaluated from the standpoint of the present invention, gel electrophoresis can provide a significantly enhanced utility. This advantage comes about in the following way.

The present invention includes a method which can resolve at least a portion of a biomolecule specifically distinguishable against chemically complex backgrounds. In one embodiment, the present invention can be used for determining a code sequence of large duplex DNA molecules in polyacrylamide gels using conventional electrophoretic equipment.

In explanation of this advantage, we note that a critical parameter that may limit the performance of present gel-based techniques is a band-broadening of DNA sequencing reactions, as they are separated through a fixed distance of gel at continuous field strengths, often ranging from 50–400 V/cm. The size-dependence of band widths may be a result of various mechanisms of reorientation and migration of the nucleic acid fragments in the gel, such as diffusion and thermal gradient broadenings.

Now, when a sample biomolecule migrates through a polymer solution chemically cross-linked, such as polyacrylamide or agarose gels, an overall friction coefficient can become a complicated function of the pore size in the gel, the size of the sample and the electric field strength, thereby limiting resolution.

Several approaches based upon the use of capillaries or pulsed fields can partially overcome this limit of resolution (C. R. Cantor et. al., Pulsed-Field gel electrophoresis of very large-DNA molecules Annual Review of Biophysics and Biophysical Chemistry, vol. 17, 287, 1988).

A spatial resolution of the detection system may also be a source of band broadening, relying on the fact that a detector does not interrogate an infinitely thin section of the sample as it reaches a finite detection volume, thereby precluding single nucleotide resolution. Present confocal-fluorescence microscopes typically provide a fat field detection system to interrogate either capillaries or slab gels with a limiting sensitivity, defined as a signal-to-noise ratio of 1, or about $10^{-17}$ mole of fluorescently labeled DNA per band and a spatial resolution ranging from 10 um (Smith L. M., et al., Nature, vol. 321, 12 June, 1986). Based upon several theoretical approaches of band broadening in sequencing analysis by gel electrophoresis (Y. F. Chen et al., Anal Chem., 62, 496–503, 1990), a theoretical peak width of a band may be determined to be a complex function of starting conditions (i.e., injection time and volume), detection (spot size of the focused laser beam), diffusion and thermal gradient variances.

Now, starting conditions begin with an injection process.

During an injection process, which comprises loading biomolecules in the gel, the biomolecules are not stacked by moving boundaries of buffet conditions, and the biomolecules therefore enter the gel at different rates corresponding to their electrophoretic velocity in the gel, thereby contributing to the net effect on the band width variance. Subsequent detection of the biomolecule may comprise using a focused laser with a Gaussian beam profile. For this situation, a standard deviation of the beam profile can be estimated to be equal to one-half the beam spot. This yields a detection variance of the form $\sigma^2 = w^2/4$, where w is the spot size. In most conventional equipment, lenses or fiber optics may be used to focus the laser on the slab gel or filled gel capillary vessel, but due to an orthogonal direction of the excitation radiation with the emitted radiation, the numerical aperture of the lens of the optical detection system may therefore be limited to about 0.20–0.75. For example, several collinear arrangements for on-column detection in capillary electrophoresis have been reported using narrower capillaries and higher numerical aperture, permitting more fluorescence to be collected, thereby contributing to sensitivity improvement.

In preparation for gel electrophoresis, a sample is loaded in each lane of a slab gel in a well of typically 0.4 mm×6 mm, or 2.4 mm$^2$, whilst for example in a 50 um capillary, the surface area of the top of the gel is one thousandth of that in the slab gel, corresponding to about $10^{-7}$ mole of sample in a given band. Accordingly, loading conditions not taking advantage of sample stacking and optical diffraction threshold of detection system may be significant sources of band broadening, affecting resolution.

In sharp contrast, the procedures and embodiments of the present invention define innovative approaches to overcoming the above limitations by employing, in a specific embodiment, a mechanism that can focus sample bands to the sample dimensions, at least 0.1 micron, and a near-field detection system that permits spatial resolution beyond the diffraction limit, thereby extending the limit of concentration detection to at least the mass of a single molecule.

One way to increase conventional gel electrophoresis low mobility is to use free-solution electrophoresis. Here, there is no dispersion in mobility with molecular length (M bases). This is clue to the fact that mobility (velocity divided by electric field) is equivalent to electric charge divided by friction coefficient, and both electric charge and friction coefficient scale linearly with molecular length, M. In Mayer et al (Anal. Chem. 1994, 66, 1777–1780), there is a proposal for attaching a large molecule at the end of each fragment in order to add a constant friction contribution to each. In this way, mobility is no longer independent of the number of bases. Theoretical calculations based on this reference suggest that dispersion can allow one to separate 3000 nucleotides in five minutes, in a best case comprising a far field detection limit.

Finally, we reference in passing proposed advanced technologies comprising large-scale automated DNA sequencing methodologies, namely, applying mass spectrometry to fast sequencing DNA, or sequencing by hybridization. See references 1) R. J. Lewis et al, J. AM. Chem. Soc., 113, 9665, 1991 and 2) R. Drmanac et al, "Sequencing of Magabase Plus DNA by Hybridization: Theory of the Method" in Genomics, vol. 4, pp. 114–118 (1989), respectively.

We have now discovered an approach to biomolecular code sequencing which is qualitatively distinct from the prior art. This different approach is manifest in a novel method suitable for identifying a code sequence of at least a portion of a biomolecule, the method comprising the steps of:

1) using a near-field probe technique for generating a super-resolution chemical analysis of the portion of a biomolecule; and 2) correlating the chemical analysis with a broad spectral content of a referent biomolecule for generating a code sequencing.

The present invention as defined can realize several significant advantages.

First of all, the novel method has an immanent capability for generating nucleotide sequencing information of such a quality, quantity and time-responsiveness, that heretofore even merely theorized applications requiring such information can now become a straightforward reality. For example, the method can be employed for developing a map that accurately reflects both individual nucleotide identification (i.e., A, G, C and T) and the location of an individual nucleotide with respect to a strand of arbitrary length, including an entire genome.

In this sense, moreover, the novel method can evince a remarkable versatility, since it may be selectively and variously employed e.g., in dependent steps, for:

1) identifying a first nucleotide from a second(adjacent) nucleotide;

or 2) locating with respect to an arbitrary strand or to a genome, a location of an identified nucleotide;

or 3) identifying a first duplet, codon, gene from a second (adjacent) duplet, codon, gene;

or 4) locating with respect to an arbitrary strand or to a genome, a location of an identified duplet, codon, gene.

To this end, the novel method has a capability for generating a fast and/or high throughput code sequence e.g., comprising at least 1000 bases/portion of biomolecule, preferably at least 100 kilobases bases/portion of biomolecule within less than 1 hour, particularly an entire human genome within less than one day, for example, 3 kilobases in less than 5 minutes.

Other advantages of the novel method proceed from the following considerations. An application of the method can generate, for the first time, nucleotide information of a quality and quantity sui generis. This information, in turn, can become a centerpiece for new and efficient approaches to gene testing or drug design, DNA sequence homology or biomolecular computing.

Other advantages of the novel method are enumerated below.

BRIEF DESCRIPTION OF THE DRAWINGS

The invention is illustrated in the accompanying drawing, in which.

and

Figure 11:
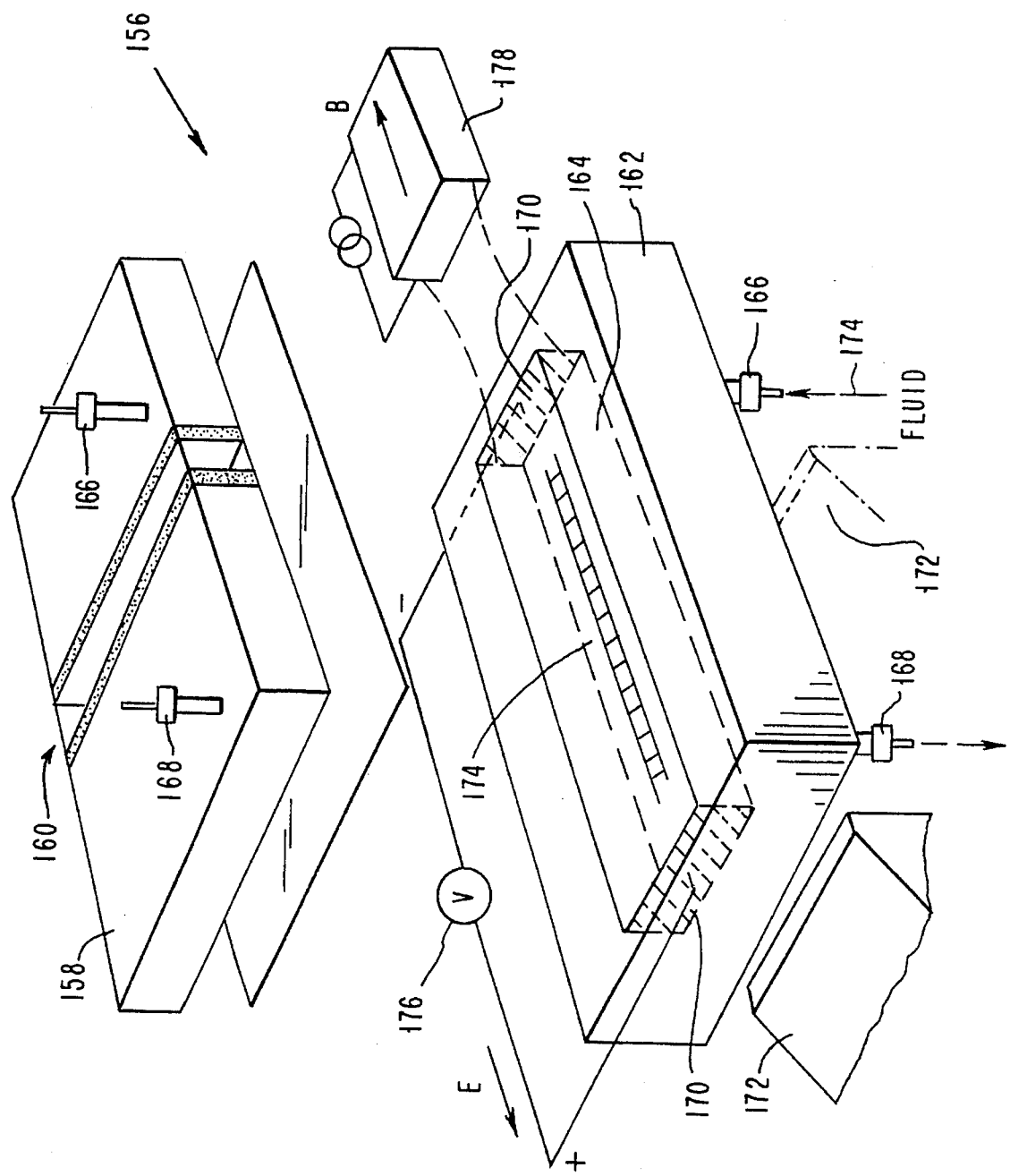
Figure 12:
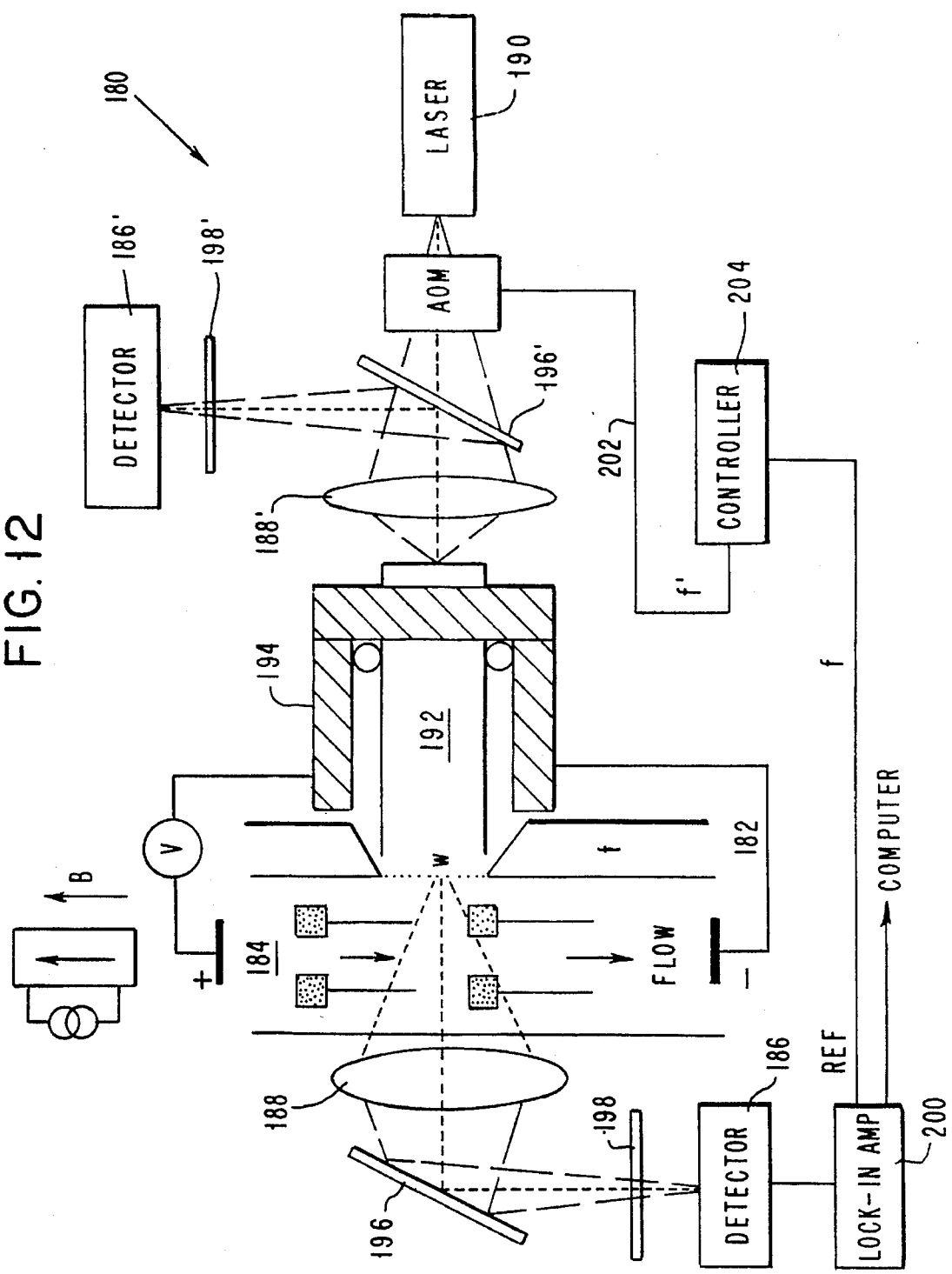
Figure 13:
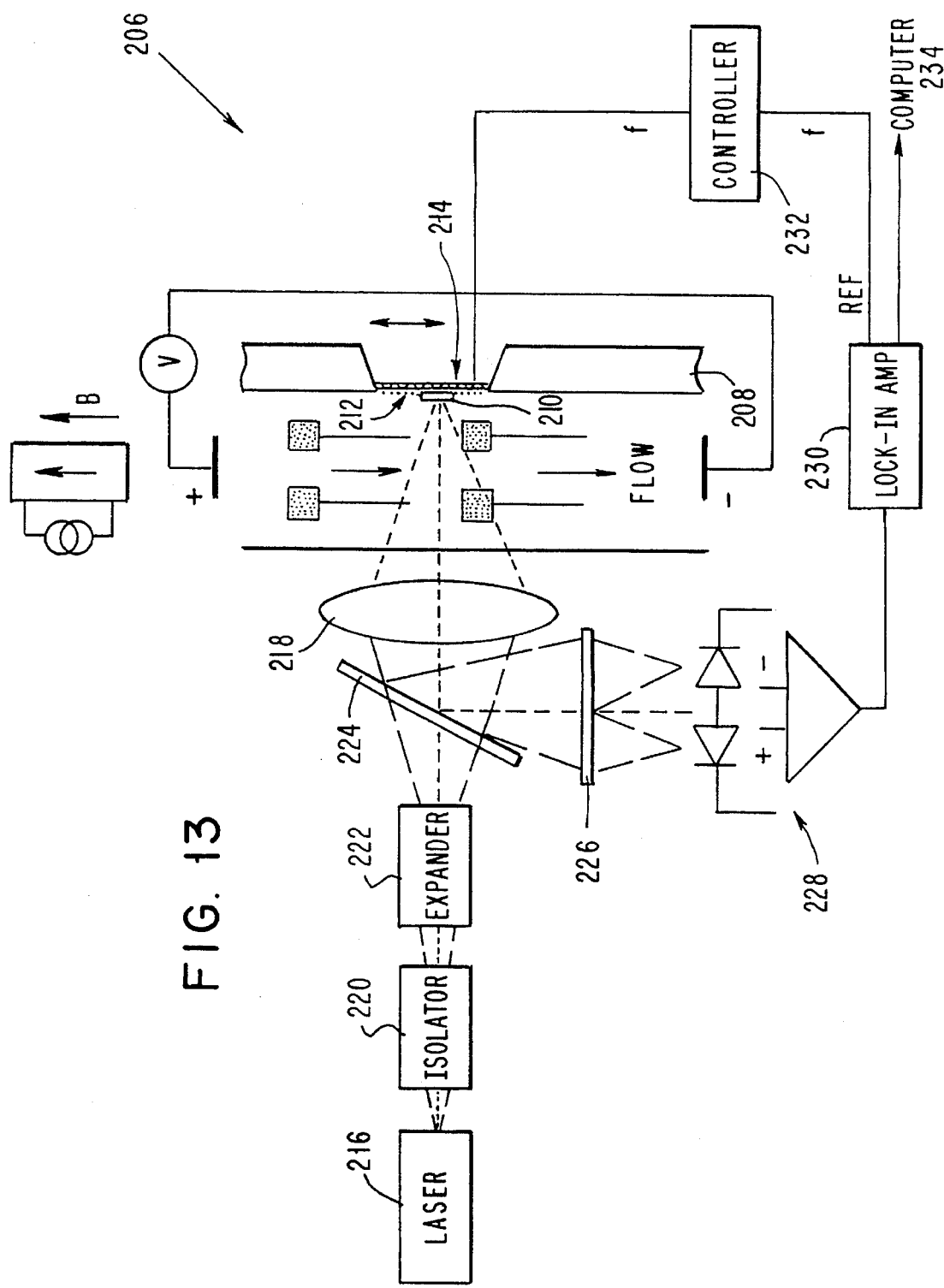

FIGS. 11–13 show further embodiments and details of systems and assemblies constructed in accordance with the present invention.

DETAILED DESCRIPTION OF THE INVENTION

In the interests of clarity, the following detailed description of the invention includes sections which are chiefly or exclusively concerned with a particular part of the invention. It is to be understood, however, that the relationship between different parts of the invention is of significant importance, and the following detailed description should be read in the light of that understanding. It should also be understood that, where features of the invention are described in the context of particular Figures of the drawing, the same description can also be applied to the invention in general and to the other Figures, insofar as the context permits.

Section one sets forth sundry definitions and examples of words, phrases or concepts that may be abstracted from the summarized invention, or may be used to reference preferred embodiments of the invention. Section two provides a conceptual overview of the present invention with special emphasis on that aspect of the present invention which comprises coupling a near-field scanning probe technique with interrogation of a biomolecule. Section three discloses in overview an assembly that may be preferably used to realize the present invention. In a fourth section, we disclose particulars of a preferred near-field probe included in the section three assembly, while in a fifth section entitled "Chemistry", we disclose preferred techniques for preparing a biomolecule for sequencing. Section six, entitled "Correlation", builds on the previous sections, and discloses how the invention can correlate a chemical analysis of an arbitrary biomolecule with spectroscopic data of a known such biomolecule. Sections seven and eight are dedicated respectively to preferred realizations of the present method in free-solution and gel. Section 9, finally, builds on the previous sections and discloses further assembly and system details.

I. Definitions

1. "a code sequence": In reference to a biomolecule, a code sequence means the order of the basic building blocks of a macromolecule or equivalent chemical compound, for example, amino acids for peptides, nucleotides for nucleic acids or a sugar residue for carbohydrates. A code sequence may comprise a map that is 1 to 1 congruent with a portion of a biomolecule i.e., endomorphic, or alternatively, may be isomorphic with respect to the portion. To illustrate this point: assume that an arbitrary nucleotide string comprises AAGCATATCG. Then, an endomorphic code sequence consists of AAGCATATCG, while an isomorphic code sequence may comprise alternative nucleotides i.e., ACTTG.

2. "a portion of a biomolecule": A biomolecule comprises polymeric macromolecules. The present method may be used to interrogate the code sequence of an entire macromolecule, or at least a preselected portion of a macromolecule. For example, the method may be used to interrogate the code sequence of a fragment of DNA.

3. "electrophoresis" comprises a separation of molecules on the basis of their net electrical charge. For purposes of the present invention, electrophoresis may be carried out, e.g., in a gel or preferably in a free-solution.

4. "near-field probe techniques": near-field probe techniques can provide a measurement modality capable of resolution of a sample beyond the diffraction limit and capable of atomic resolution imaging. In brief, the technique may comprise placing a subwavelength-sized probe within tens of nanometers of the sample: Travelling over such short distances, radiation has no opportunity to diffract and take on its asymptotic far-field characteristics—hence the name "near-field". Note that a suitable probe may comprise a sharp metallic tip or an uncoated silicon and/or silicon nitrate tip, or a tip coated with a conductive layer or a molecular system. A near-field probe capability may be realized by e.g., a scanning tunneling microscope (STM), an atomic force microscope (AFM), an aperture or apertureless near-field optical microscope, a near-field acoustic microscope, a thermal microscope or a magnetic force microscope (MFM). The notion of "scanning" references the fact that probe and biomolecule may be in relative motion. Reference may be made for example to U.S. Pat. Nos. 5,319,977; 4,343,993; 5,003,815; 4,941,753; 4,947,034; 4,747,698 and Appl. Phys. Lett. 65(13), Sep. 26, 1994. The disclosures of each of these patents and publications are incorporated herein by reference.

5. "super-resolution chemical analysis" comprises a recognition of a chemical species e.g., at least a portion of a biomolecule, by analyzing a molecular specificity of its spectra or pints thereof, preferably by using spatially resolved spectroscopy with physical methods, for example, near-field microscopic techniques.

6. "broad spectral content of a biomolecule" means a characterization of a spectra e.g., absorption or emission or thermal or magnetic properties of a pre-defined analyte when it is preferably interrogated by a tuned excitation radiation source with a frequency specific to an analyte being monitored, ranging from x-ray, UV, visible, IR or microwave of the spectrum.

II. Conceptual Overview of Present Invention

As alluded to above, the present invention comprises coupling a near-field probe technique with interrogation of at least a portion of a biomolecule to an end of generating a super-resolution chemical analysis of a portion of the biomolecule under interrogation, and correlating the chemical analysis with a broad spectral content of a referent biomolecule for generating a precise code sequencing.

If even theoretically contemplated, it is not technically known or obvious outside of the present instruction, how one may effect the required coupling. Restated, the desired result i.e., the precise code sequencing, cannot in fact be effected by some sort of nominal juxtaposition of a near-field probe and a biomolecule. (cf. imaging). We note that the reason for this is that a putative such attempt simply results in a blurred and information-less output signal.

The present invention addresses and solves this problem by way of preferred novel assemblies suitable for identifying a code sequence of at least a portion of a biomolecule. Various preferred embodiments of these assemblies are disclosed below.

III. Overview of Physical Components of Invention As An Assembly

Figure 1:
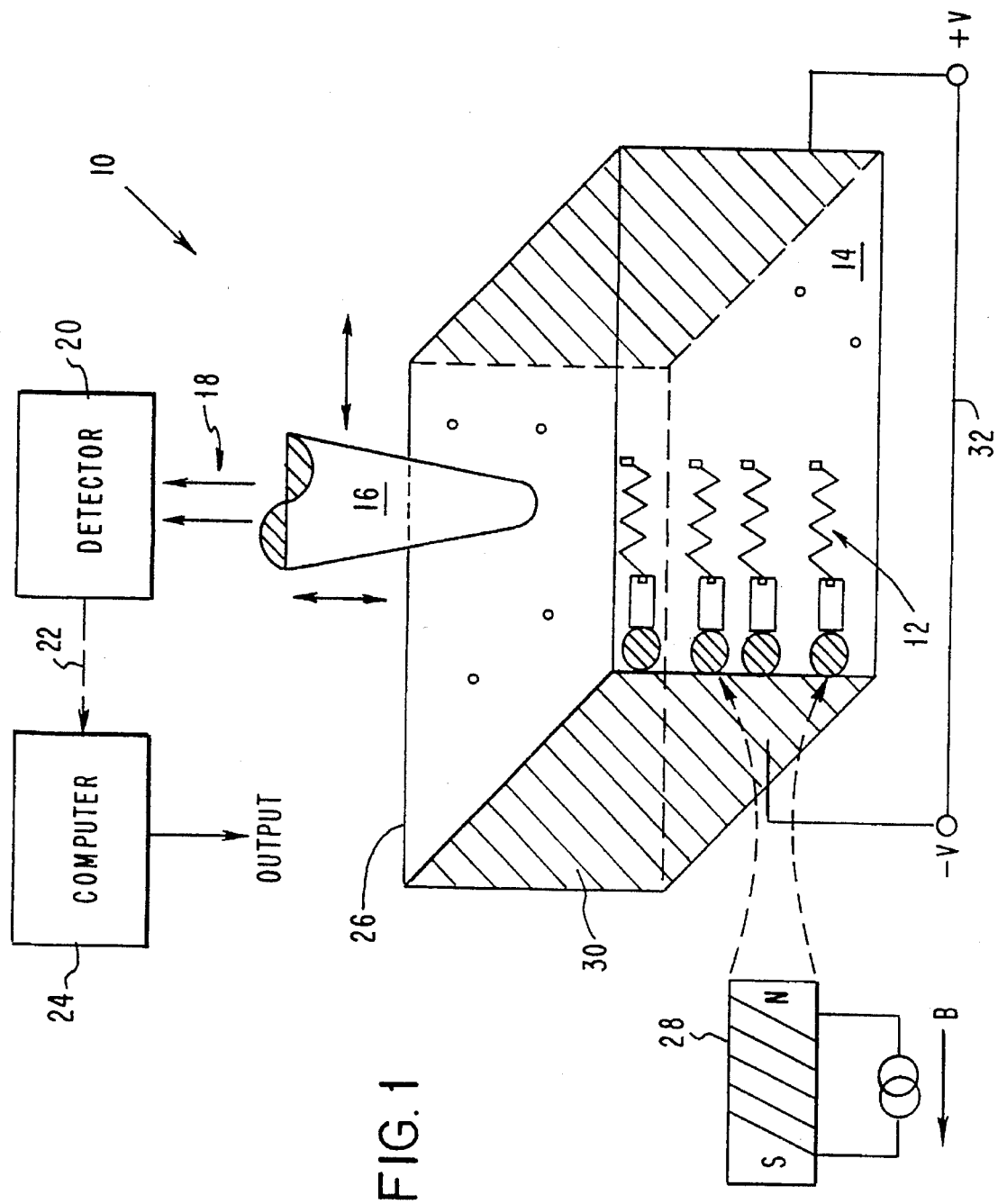
FIG. 1 shows an assembly suitable for identifying a code sequence of at least a portion of a biomolecule, and of utility in realizing the novel method.

Attention is now directed to FIG. 1, which shows a schematic overview 10 of physical components that preferably may be assembled in realization of the present invention, in particular, for distinguishing a biomolecule 12 against a chemically complex background solution 14.

The biomolecule 12 can migrate beneath an interrogating and preferably movable i.e., scanning (see arrows) near-field probe 16. Note that FIG. 1 shows one such near-field probe. However, expediencies of interrogation may be realized by suitably ganging a plurality of near-field probes. Note that the near-field probe 16 can function as an excitation source, or alternatively, an external excitation source (see FIGS. 8, 10, 12, 13 infra) can be used.

A resultant interrogation signal 18 from the near-field probe 16 may be detected by a detector 20, comprising, For example, a conventional spectrometer e.g., an interferometric system. The detector 20 can generate a detection signal 22 for storage and processing on a computer 24. For example, an IBM RS 6000 may be programmed for interpreting a sequence of building blocks of a biomolecule comprising amino acids in a case of proteins, or nucleotides in a case of nucleic acids.

Note in FIG. 1 that the biomolecule 12 is initially loaded in a container 26 comprising the solution 14, preferably using a stretching procedure comprising external radiation such as a magnetic field 28, and a specific positioning of the biomolecule 12 to a support 30. This arrangement can facilitate an efficient immobilization and stretching of the biomolecule 12, for example, before and during the migration rate, by way of an applied electric field generated by a power source 32. These points are amplified below, in section V entitled "chemistry".

IV. Preferred Near-Field Probe and Detection

FIG. 1 indicates the employment of a near-field probe 16 and an excitation source and a detector 20. Further information on preferred such devices is now set forth by way of FIGS. 2,3.

Figure 2:
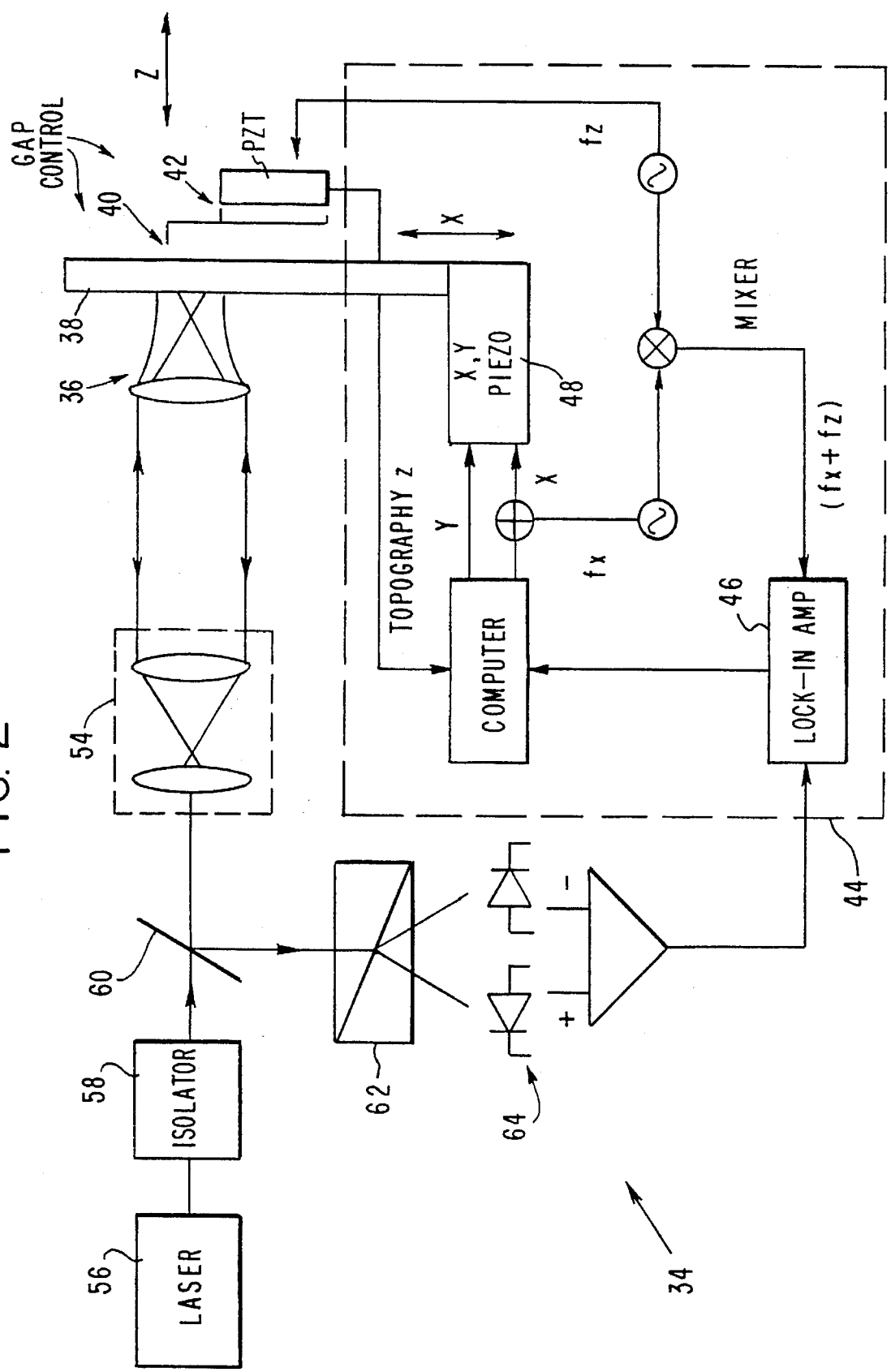
FIG. 2 shows a near-field scanning probe comprising an apertureless near-field optical microscope.
Figure 3:
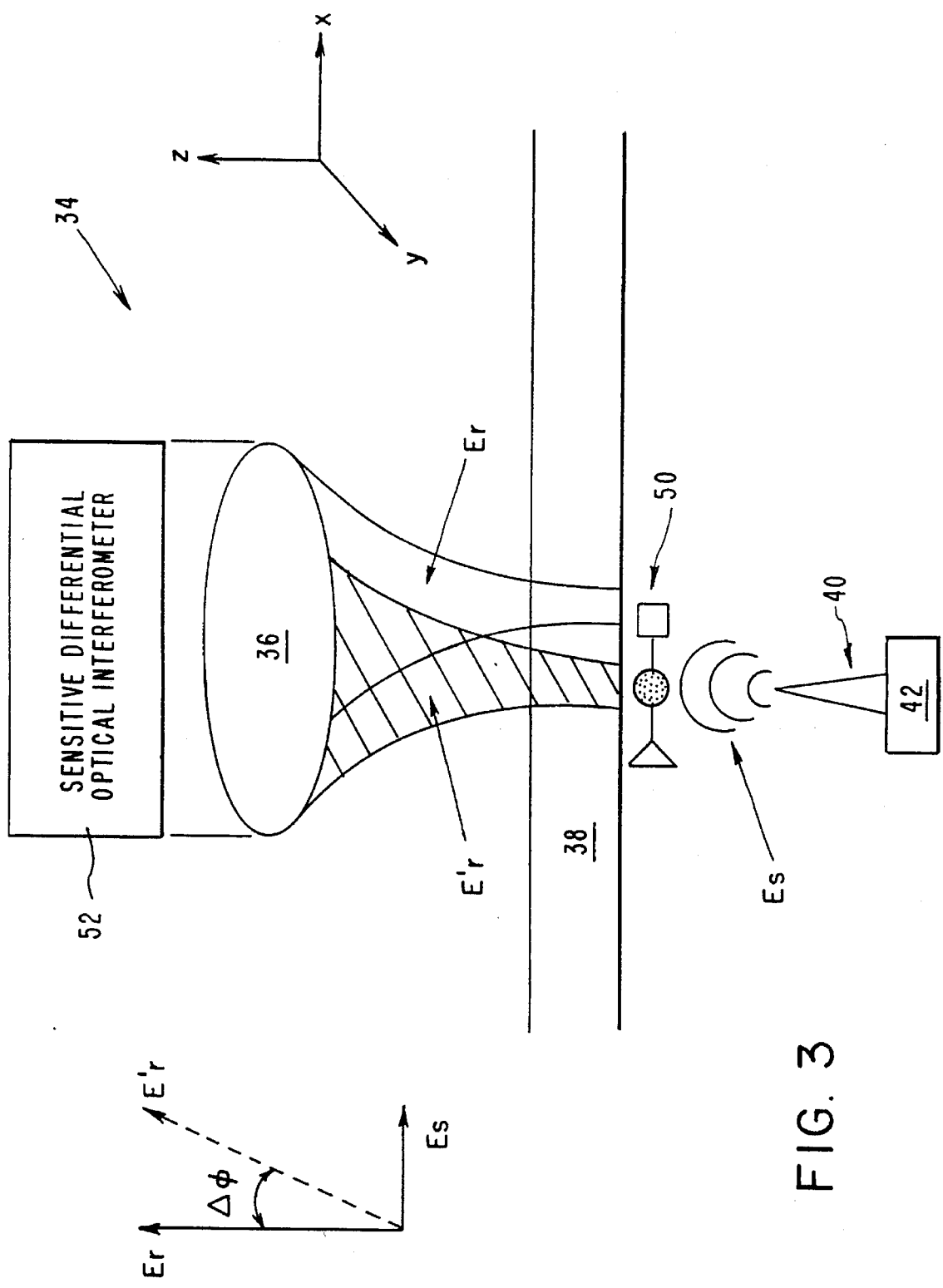
FIG. 3 provides a schematic for explaining basic concepts about the FIG. 2 apertureless microscope.

A preferred apertureless near-field scanning probe microscope and detector 34 are shown respectively in FIGS. 2, 3. The apertureless near-field scanning microscope is preferred because, among other reasons, its capability of measuring absorption properties of a sample can be extended to a spatial resolution in the sub-nanometer regime, thereby realizing single nucleotide resolution (cf. nucleotide length α1 to 2 angstroms). We note that aperture based systems can also be used, at lower resolution e.g., approximately λ/40. In particular, the FIGS. 2, 3 microscope comprises an apertureless near-field optical microscope wherein a light source preferably emits spherical light scattering from a sharp tip, rather than light transmitted through a fine aperture.

An understanding of the operation of the .FIGS. 2, 3 apertureless microscope 34 is now provided by first summarizing :its mechanical-physical components, and then disclosing its theory of operation.

The microscope preferably includes a high numerical aperture Nomarski objective 36 (e.g., liquid immersion objective)that may be used to form two diffraction limited spots at the far surface of a transparent substrate e.g., a glass cover slip 38. A sharp silicon tip 40 of an AFM cantilever 42, appropriate for non-contact or tapping mode, may be approached toward one of the two spots using an independent electronic feedback loop 44.

We preferably use an attractive mode AFM in the "tapping mode" to perform the gap feedback. In this mode, the resonating cantilever 42 at e.g., resonant frequency $f_r$ may be made to move toward and away from the sample (using a piezoelectric transducer PZT) at a frequency $f_z$ which is typically much lower than the resonance frequency $f_r$. The vibration signal at $f_r$ may be detected in a lock-in amplifier 46, and its average value may be used in the feedback loop 44 to control tip-sample spacing. By adjusting a piezodrive amplitude 48 at frequency $f_z$, we can change the tip/sample interaction conditions from hard tapping to soft tapping or true non-contact imaging.

A theory of operation of the microscope may be developed as follows. In general, as shown in FIG. 3, a biomolecule 50 placed in close proximity of the probe tip 40 can be interrogated by measuring a modulation of a scattered electric field from the end of the probe tip 40.

In particular, a reflected electric field from the spot that impinges on the probe tip 40 comprises two components: a weak scattered field $E_3$ from the probe tip 40 and a strong reflected field $E_R$ from the back surface of the cover slip 38 (see FIG. 3). The reflected field $E_R$ is phase advanced by $\pi/2$ relative to the scattered field $E_s$ due to the Gouy shift through a focused Gaussian beam. For small amplitudes of scattered light, the overall phase $\angle E'_r$ of the reflected beam from the spot that impinges on the probe tip is phase delayed by $\Delta\phi = E_s/E_r$, relative to the phase of the second reflected optical spot of amplitude $E_r$. The scattered field $E_s$ from the tip end can therefore be deduced directly by measuring $\Delta\phi$ in a sensitive differential optical interferometer 52. Features on the back surface of the coverslip i.e., the biomolecule 50, modulate $E_s$ as the biomolecule 50 is raster scanned relative to the probe tip 40. These variations may be recorded sequentially on a computer in order to generate the data for generating a super-resolution chemical analysis of the biomolecule 50 which will be used for generating its code sequence. (See discussion Section six, infra.)

The scattered field $E_s$ from the probe tip end will in general be present on top of a spurious background of light scattered from the tip shank and cantilever 42. We can reduce the background signal in three ways. First, as shown in FIG. 2, we preferably use a confocal arrangement 54 for optical illumination and detection; this can restrict the detection region to within 100 nm of the tip end. Second, we realize that if we modulate the tip in z at frequency $f_z$ by an amplitude which is approximately the tip radius, the backscattered light from the tip end can have a larger modulation on the biomolecule as compared with light scattered from regions that are farther away, as we approach the tip very close to the sample. Finally, we can further enhance the signals at the spatial frequencies of interest (i.e., corresponding to the radius of the tip) by vibrating the biomolecule laterally by approximately the tip radius at frequency $f_x$ and detecting the interferometer signal at the sum frequency $(f_x + f_z)$.

Further shown in FIG. 2 is a laser 56 preferably radiating vertically polarized light that may be serially directed toward the Nomarksi objective 36 via an isolator 58 (which rotates the polarization by 45°), a beam splitter 60 and the spatial filter 54. The objective 36 can focus the light to two diffraction limited spots on the back surface of the cover slip 38. The reflected light from the two spots can return via the pin hole onto the beamsplitter 60, which can direct it onto a Wollaston 62 used as an analyzer and whose axis preferably can be arranged at 45° to that of the Nomarski objective 36.

The two spots emerging from the Wollaston 62 may then be detected in a differential photodiode arrangement 64 in order to yield a signal proportional to the phase difference $\Delta\phi$. The operating principles of such differential interferometers are well known and will not be described here. For typical laser powers in the mW range, the smallest detectable phase difference $\Delta\phi$ is on the order of $10^{-8}$ rad/$\sqrt{Hz}$.

We can estimate the ultimate resolution that may be achieved with our apertureless microscope 34 by using some simple considerations. If we approximate the tip end to be a sphere of radius a, and assume an incident electric field. $E_i$, the scattered spherical wave has an amplitude $E_s = E_i k^2 \alpha/4\pi$, where k is the optical propagation constant in air and $\alpha$ is the susceptibility of the sphere given by $$\begin{bmatrix} \alpha_\| \\ \alpha_\perp \end{bmatrix} = 4\pi a^3 \frac{(m^2-1)}{(m^2+2)} \begin{bmatrix} (\cos\theta)_\| \\ (I)_\perp \end{bmatrix} \quad (1)$$

Here, m is the complex refractive index of the sphere, and the polarizability must be chosen depending on the incident wave polarization direction relative to the scattering angle $\theta$. The reflected wave from the cover slip 38 is a concentric spherical wave of amplitude $E_r = (E_i/5)(\omega_0/NA)$, where $\omega_0 = \lambda/\pi NA$ is the optical spot radius and NA is the numerical aperture of the objective lens 36. The expected phase difference $\Delta\phi$ between the two spots is then simply $E_s/E_r$, or $\Delta\phi = 5k^3\alpha NA^2/8\pi$. Taking a silicon or metal tip (i.e., $m^2 \gg 1$) of radius a and $\alpha_\|$, we have, $$\Delta\phi \approx \frac{5}{2} k^3 a^3 NA^2.$$

For a coherent, shot noise limited phase detection system with mW laser power, we can show that $\Delta\phi_{min} \approx 10^{-8}$ rad/$\sqrt{Hz}$. This would suggest that for He-Ne laser light ($\lambda=633$ nm) with NA=0.85, $\alpha \approx 1.7$ Å, i.e., the resolution reaches single nucleotyde detection and even the atomic level.

V. Chemistry

Attention in this section is directed to preferred procedures for preparing a biomolecule, for example DNA, for sequencing in conjunction with separation by electrophoresis and detection by a near-field probe.

A separation of large molecules preferably is based on a modification of electrophoresis in free aqueous solution. Here, the electrophoretic velocity is dependent on the ratio of an electrical force and a frictional force. For example, since a duplex DNA strand bears an effective charge of at most 0.5 electron per base pair, the electrical force on the molecule is also constant per unit length, and thus the electrophoretic velocity can only be dependent on size e.g., by an addition of a monodisperse or protein chemical with high friction coefficients (for example, streptavidin), since this action is most favorable for additional friction to manifest. A subsequent attachment of the end-labeled macromolecule to a magnetic molecule or microsphere can provide a preferred means of manipulating the molecules by an external magnet, as starting and advancing together, thereby resulting in a higher resolution of the separation step. Separation speed and resolution are dependent on factors controlling bandwidth.

Figure 4:
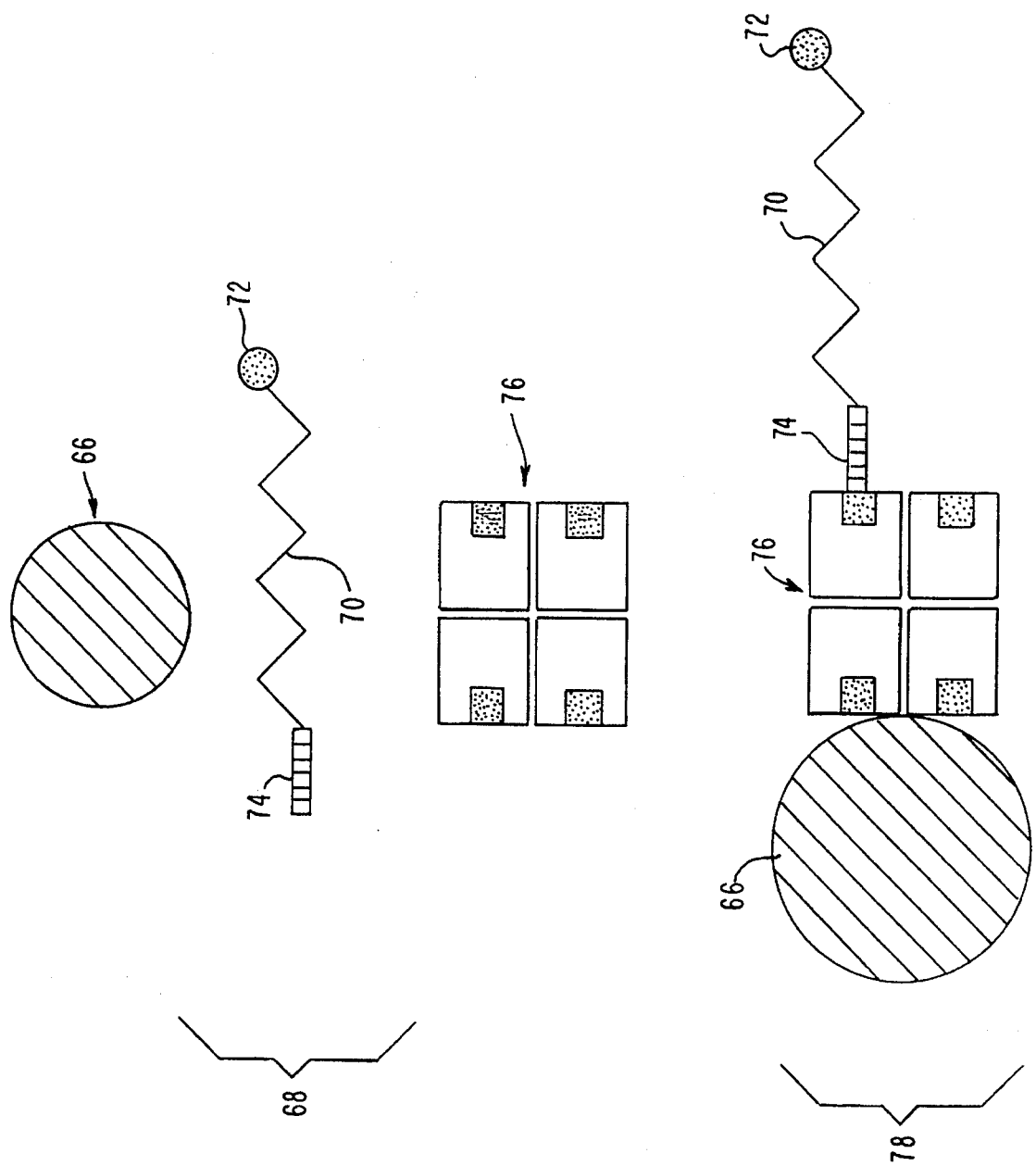
FIG. 4 shows a chemical modification of a biomolecule into a sample preliminary to its interrogation by a near-field scanning probe.

In accordance with the above arguments, this invention provides a mechanism for controlling the initial conditions of the electrophoresis, for example as sample loading, employing specific chemical methodology. To this end, FIG. 4 illustrates in principle how we propose to thether and then align a biomolecule for focusing a band in the range of the sample dimensions. In the case of DNA, fragments, typically from a few bases to an entire genome, may be made by using all of the current strategies for obtaining products of sequencing reactions. In FIG. 4, magnetic monosized particles or beads 66, For example, ferritin or Dynabeads,™ respectively, can be used to immobilize a sample 68 onto the surface of a substrate (not shown) thereby allowing positioning and extending of the molecule under the strength of combined static electric and magnetic fields. A FIG. 4 sample 68 comprises an end-labeled biomolecule 70 having an absorbant tag 72 at one end, and an anchoring chemical 74 e.g., a biotin at the other end.

When a strong electric field (for example $10^6$ V/m or up to the limit of the dielectric breakthrough of the solution) is switched on, the migration rate of the sample is retained, linear and distinguishable from random Brownian motion, by applying a stretching electromagnetic Force necessary to straighten DNA molecules, for example, as long as genomic DNA. This step can be performed by using the method or derivatives recommended by the manufacturer in the Dynabeads preparation kit (Dynal AS, Oslo, Norway) or by other equivalent published methods.

The FIG. 4 sample 68 can be conjugated to the magnetic particles either covalently (via carboxyl-, hydroxyl-, or amino groups on the solid surface) or non-covalently by streptavidin-biotin interactions types (particles coated with streptavidin 76), thereby building a complex chemical assembly 78.

In this case, the FIG. 4 streptavidin 76, a protein with four high affinity binding sites for biotin, may be reacted with biotinylated DNA fragments (for example, prepared by PCR). Due to a strong binding constant of the complex biotinstreptavidin (i.e. $K_d < 10^{-15}$M), this bond is resistant to various buffer conditions and to the stretching force in an alignment process. For long nucleic acids, typically double stranded DNA, better coupling may be obtained respectively by carbodiimide-mediated end- attachment of 5' phosphate and 5' $NH_2$ modified nucleic acids to amino- and carboxyl beads, with a success of 20–65% of DNA end-attached.

By an appropriate choice of coupling conditions, and another covalent end-attachment of nucleotides to magnetic particles e.g., via urethane type of linkage, yields to 100% end-attachment of the sample 68 to the support particles 66 can be established, as it is described by V. Lund et al., in Nucleic Acid. Res., 16(22), 10861–80, 1988.

In addition, an appropriately biotinylated sample, for example, with unknown size-distribution, may be treated by staining with an absorbant dye, binding preferentially at least to A-T pairs and G-C pairs in the case of DNA. Labeling with fluorescent dyes requires that they are compatible with broadband excitation sources, preferentially having high quantum yields and extinction coefficients for a resultant high sensitivity. In this context, current commercial methodologies may be readily utilized. A sequence-independent staining can be realized when the distinguishable chemical species, for example, an amino acid or oligonuclcotide, is measured through its absorption properties as a function of the wavelength.

VI. Correlation

The present invention comprises a step of correlating a super-resolution chemical analysis of a portion of a biomolecule, (provided by way of using a near-field probe technique), with a broad spectral content of a referent biomolecule, for thus generating a code sequencing. We now discuss this step in overview and then in detail, accentuating the concept included in the limitation "correlating", and with reference to illustrative FIGS. 5,6 and. 7.

In overview, we first address an analeptic problem— namely, the "whence", the "how", and the "what" of providing a broad spectral content of a referent biomolecule.

With respect to the "whence", we hole that the broad spectral content of a referent biomolecule may be derived from that of an arbitrary biomolecule that itself is being interrogated by way of a near-field probe, and therefore may act as an internal referent. Alternatively, however, the broad spectral content of a referent biomolecule may be derived from that of an independent or second known biomolecule.

With respect to the "how", we note that a broad spectral content of a referent biomolecule may be generated by a near-field or a far-field technique—whichever is commercially pragmatic.

With respect to the "what", we note that, on the one hand, if the near-field probe is used to generate a super-resolution chemical analysis of a portion of an arbitrary biomolecule comprising e.g., respectively, absorption or emission or thermal or magnetic characteristics, then, on the other hand, a broad spectral content of a referent biomolecule preferably is of such a related (preferably, identical) characteristic i.e., absorption or emission or thermal or magnetic, that a meaningful or viable correlogram may be constructed based upon common such characteristics.

Figure 5:
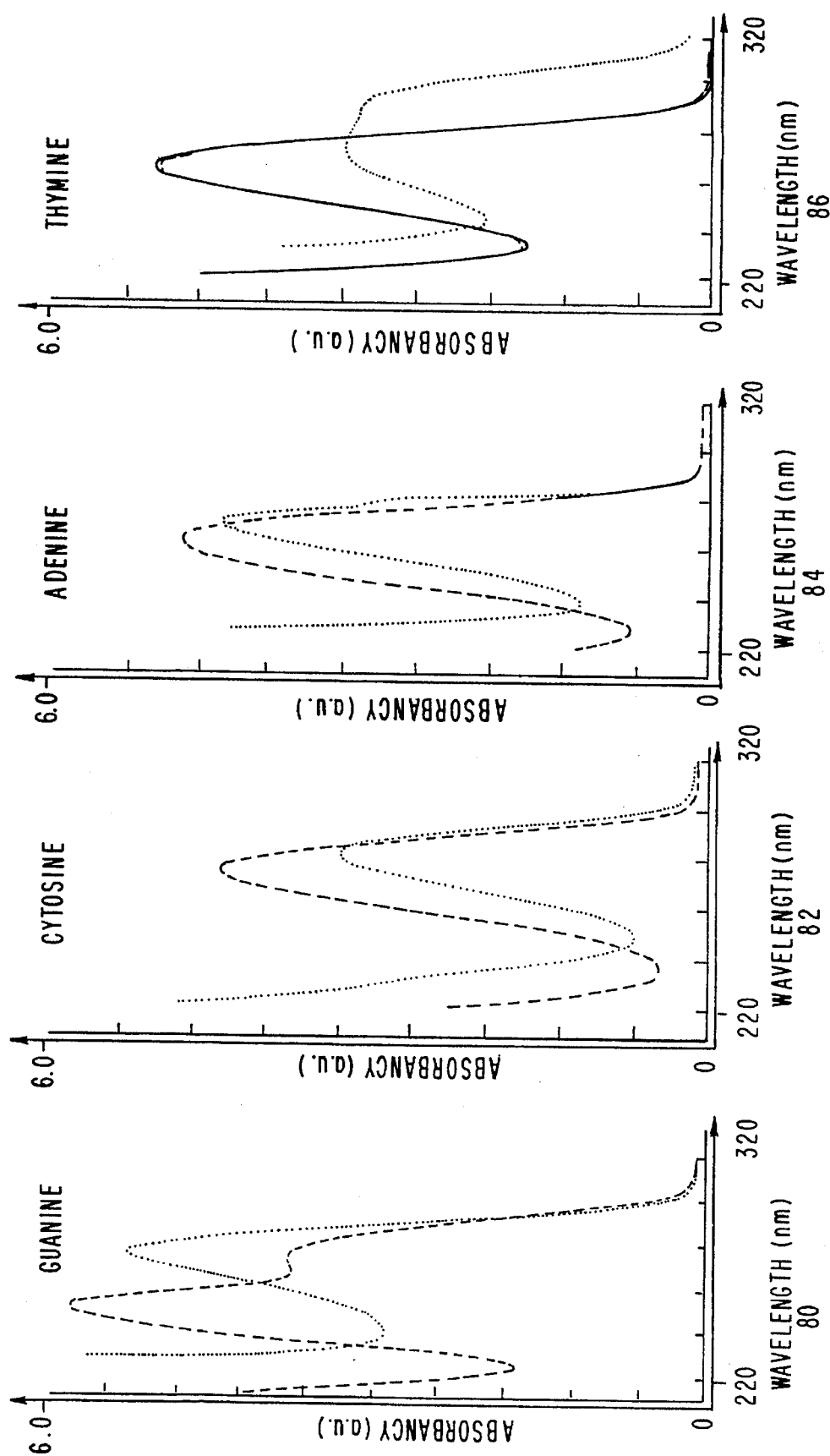
FIG. 5 shows spectroscopic curves for DNA nucleotides.
Figure 6:
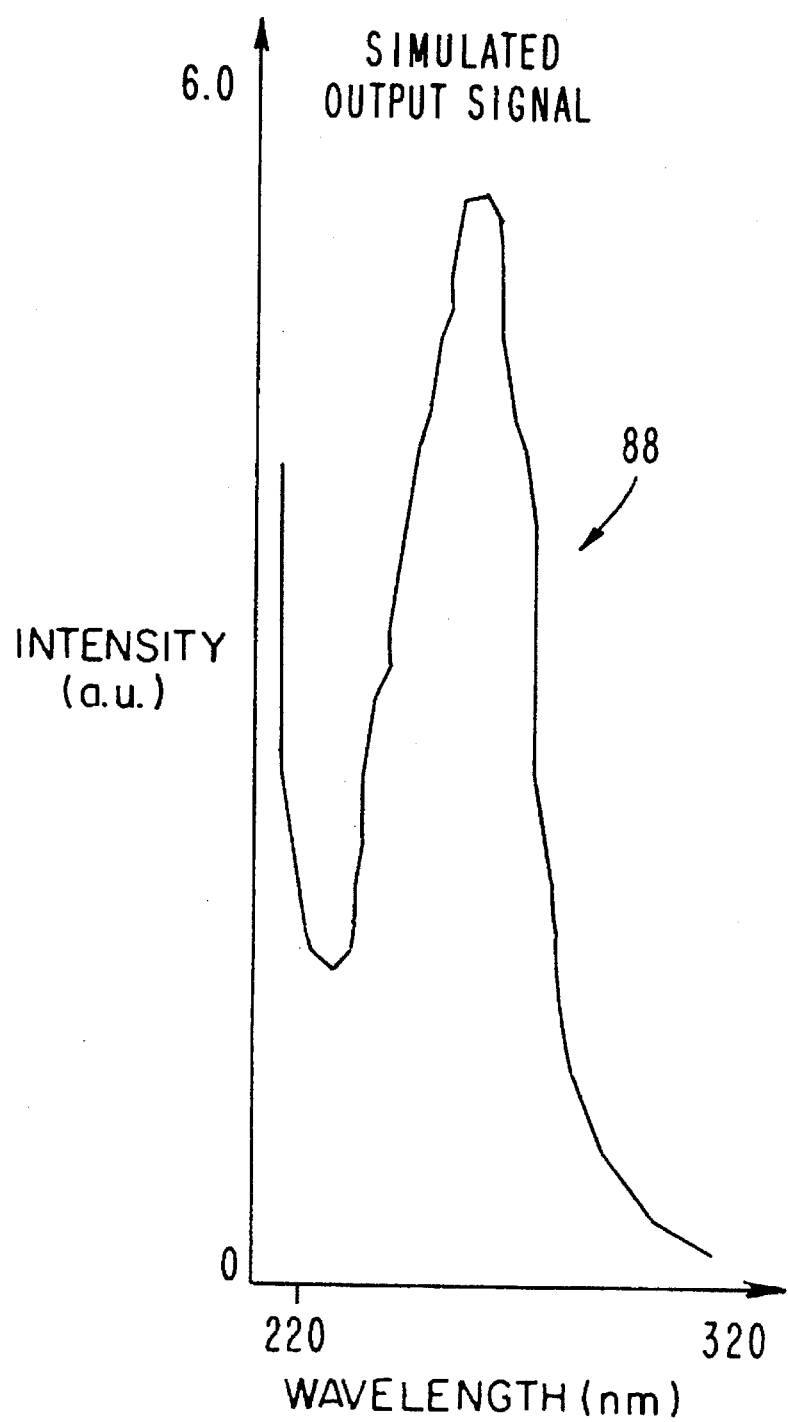
FIG. 6 shows a spectroscopic curve for an arbitrary biomolecule.

In detail and by way of example, FIG. 5 shows referent spectroscopic data (from Handbook of Biochemistry and Molecular Biology, Nucleic Acids, Vol. I, Gerald D. Fasman, CRC Press) comprising absorption spectra 80,82,84,86 for the four building blocks which make up biomolecules comprising DNA, namely, guanine, cytosine, adenine and thymine. As just explained, these spectra may be derived from near-field or far-field techniques, whichever is commercially pragmatic. FIG. 6 shows an output signal 88 (provided by way of using the near-field scanning probe technique) and comprising arbitrary spectroscopic data. The step of "correlating" comprehends establishing or mapping an identification of the FIG. 6 output signal 88 to the referent spectroscopic data 80–86. In this case, the FIG. 6 output signal 88 uniquely maps to the FIG. 5 data 86 i.e., thymine, as shown in FIG. 7 by way of a correlogram 90.

Figure 7:
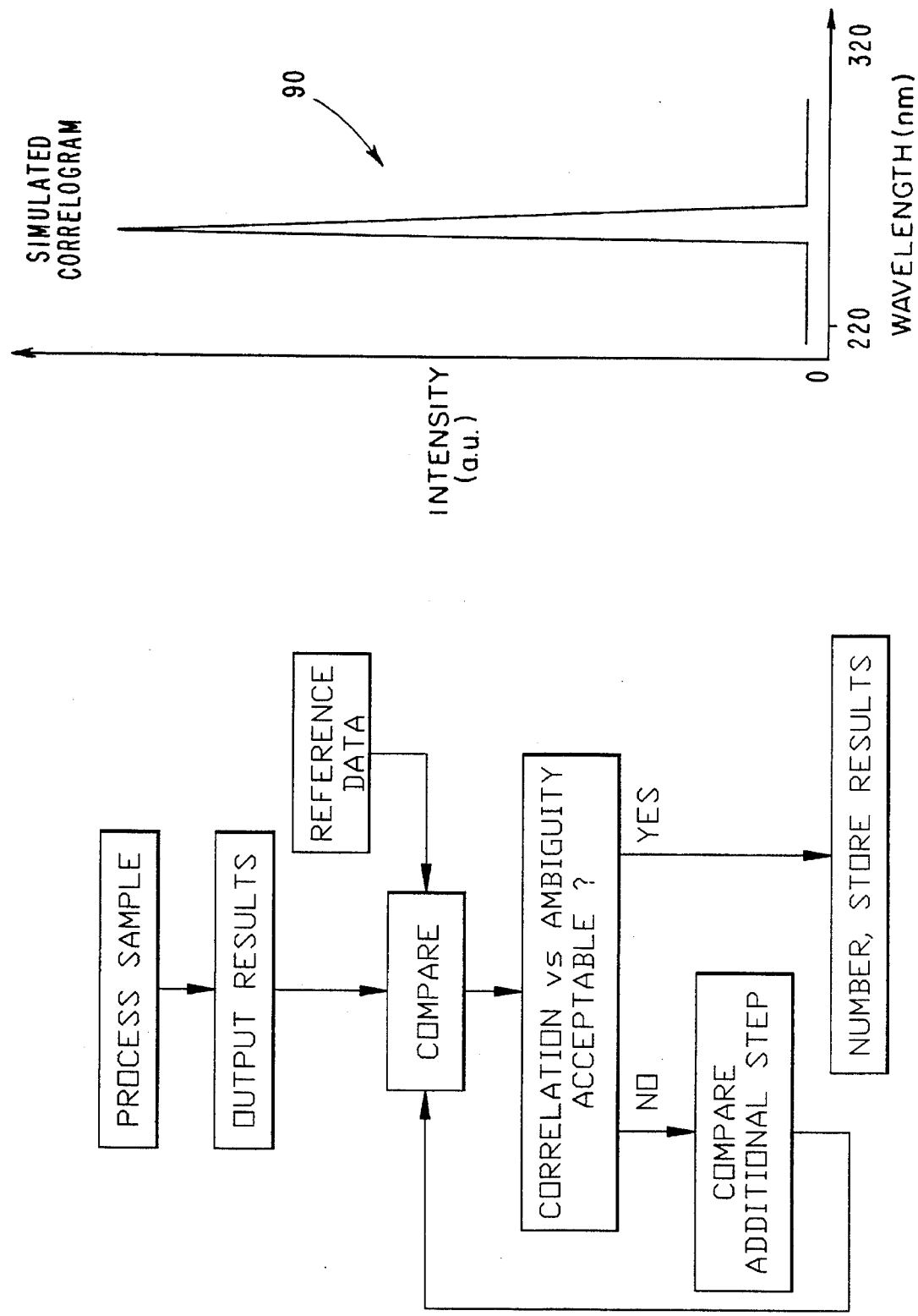
FIG. 7 shows a correlogram based on FIGS. 5,6.

As illustrated in the FIGS. 5–7 example, we may define "correlation" as an association between a referent and a sample data set which are spectroscopically quantitative and/or qualitative in nature. The analysis process may be illustrated by FIG. 7, which shows a general test: whether there is an association of some kind between the referent and measured sample date.

The whole correlation process, starting from the reading of output results, may be continued by a calculation of a correlation coefficient representing an equivalence of the two data sets, with an accuracy preferably chosen to be >95%. If and when an ambiguity is produced, the output may be returned to the correlation process via additional steps in order to yield data statistically suitable for indexing data, for example, as spreadsheet numbers or as a correlogram plotting successive correlation.

When a sequence of a biomolecule is generated, the sequence can be manipulated in various ways to gain biological information, such as in the case of gene-mapping or to match amino acid sequences on proteins. A detection of homologies (similarities) between biomolecules or portion of a biomolecule, or the detection of any pattern of a biomolecule may preferably be achieved by using an algorithm based upon those described in commonly assigned. U.S. Ser. No. 923,203, filed Jul. 31, 1992, and incorporated by reference herein.

VII. The Invention In a Free-Solution Embodiment

Figure 8:
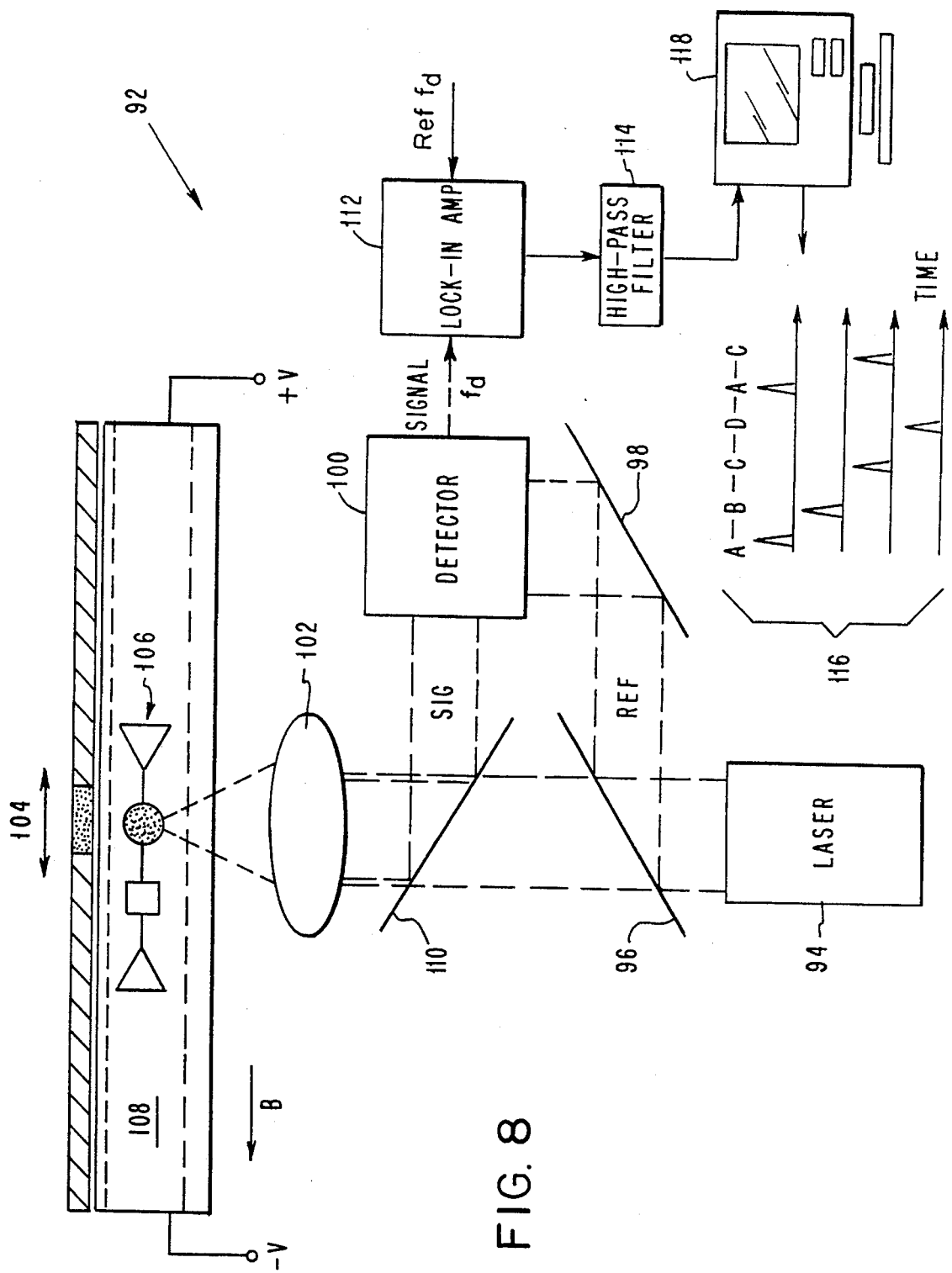
FIG. 8 shows an assembly employed to realize the invention in a free-solution embodiment.

Attention is now directed to FIG. 8, which shows an assembly 92 that preferably is employed to realize the present invention in a free-solution embodiment.

The assembly 92 includes an excitation source 94 preferably comprising a CW or pulsed laser with tunable frequency in UV, visible or IR part of the spectrum. The source 94 preferably transmits an optical energy through a first beam splitter 96, thereby dividing the incident beam into reference and signal beams. The reference beam preferably is directed through a mirror 98 to a detector 100 such as an interferometer. The signal beam preferably enters an objective lens 102 preferably comprising a liquid immersion lens, which preferably can be collinearly arranged with an oscillating near-field probe 104 and a chemical absorbant species 106 comprising a biomolecule.

During a free-solution electrophoresis, the species 106 can be monitored while it is migrated in a liquid stream through or along a fluid channel 108. A scattered field generated by the sample interacting with an evanescent field diverging from the end of the probe 104 can be serially propagated into the far field through the objective 102, a beam splitter 110, and then combined with the reference beam in the interferometric detector 100, where the fields may be detected by measuring an amplitude or phase of the combined beams.

The detector 100 can yield a signal at a dithered frequency $f_d$ which can be connected as one input to a lock-in amplifier 112. The other input of the lock-in amplifier 112 can be a reference signal at frequency $f_d$. The lock-in amplifier 112 can provide an output signal representative of the optical properties of the sample species 106, which is then preferably filtered by means of a high-pass filter 114, in order to reduce the background signal by selecting the high spatial frequencies. The measured signal variations can be recorded with time in order to spatially separate the successive signal detections of the various migrating species so that a biomolecular sequence 116 can be readily read, stored and/or manipulated in a computer 118, as shown in FIG. 8.

In order to provide a better understanding of the present invention, the mathematical relationship combining free-solution electrophoresis and near-field detection is explained below, in conjunction with 5FIG. 9. The basic concept of near-field detection relates to the method described in the U.S. Pat. No. 4,947,034, Aug. 7, 1990 and incorporated by reference herein.

Figure 9:
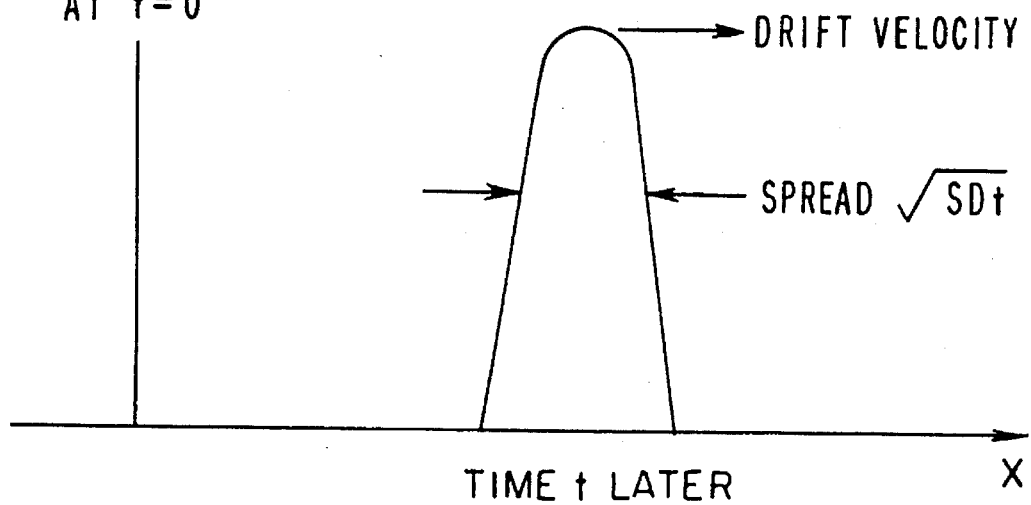
FIG. 9 shows a mathematical relationship of biomolecular diffusion actions in a FIG. 8 context.

In accordance with FIG. 9, we assume ideal starting conditions—i.e., all molecules start exactly at the same plane (i.e., δ function in x). In the presence of an electric field. E, the molecules drift with a velocity V(M) which depends on the length M of the molecule. At the same time, the bands spread out due to diffusion (diffusion constant D). We can therefore calculate a time (t) necessary to separate bands containing two lengths of molecules M and M+1:

$$v = \mu(M)E$$

In the case of an end-labelled DNA complex, as described in section V, FIG. 4 supra, the mobility of such a complex in free solution is a function of a friction coefficient $\alpha$ and an effective charge $\beta$ due to the end-label. In view of the following discussion, the free-solution mobility can be expressed as:

$$\mu = \mu_0 \frac{(M-\beta)}{(M+\alpha)}.$$

Thus, $$\frac{\partial v}{\partial M} = E \frac{\partial \mu}{\partial M}$$

$$\delta v = E \frac{\partial \mu}{\partial M}$$

where $\mu(M)$ is the mobility and $\delta v$ is the difference in velocity for two molecules of lengths M and M+1. For the two bands to separate, the spread $\delta x$ due to diffusion ($\sqrt{SDt}$, where S is a constant of order ten) must be inferior or equal to the spread caused by the velocity dispersion $\delta v$, i.e.,:

$$t \cdot \delta v = \sqrt{SDt}$$

where a diffusion coefficient is $$D = \frac{\mu_0 K_B T}{\rho(M+\alpha)} \quad (1)$$

and $$t = \frac{SD}{\delta v^2}$$

or $$t = \frac{SD}{\left(E \frac{\partial \mu}{\partial M}\right)^2}.$$

The lengths needed for separation can be expressed by the following equations:

$$L = vt = \mu E \frac{SD}{\delta v^2} \quad (2)$$

or $$L = \frac{\mu SD}{E} \left[ \left( \frac{\partial \mu}{\partial M} \right) \right]^{-2}.$$

The diffusion spread is:

$$\delta x = \frac{SD}{\delta v} \quad (3)$$

$$\delta x = \frac{SD}{E} \left[ \left( \frac{\partial \mu}{\partial M} \right) \right]^{-1}.$$

If we choose the starting conditions where the width of a band is $\omega_0$ instead of zero, we can write:

$$\delta x = \sqrt{SDt} \left[ \left( 1 + \frac{w_0^2}{SDt} \right) \right]^{1/2}$$

and going through the same arguments as previously demonstrated, we have:

$$L = \frac{\mu SD}{2E \left[ \frac{\delta \mu}{\delta M^2} \right]} [(1 + (1+\gamma^2)^{1/2})] \quad (4)$$

where:

$$\gamma = \frac{2E w_0}{SD} \left( \frac{\partial \mu}{\partial M} \right)$$

-continued with:

$$\frac{\partial \mu}{\partial M} = \mu_0 \frac{(\alpha+\beta)}{(M+\alpha)^2}.$$

For large molecules, $\gamma \ll 1$, we have:

$$L \approx \frac{Sk_B T (M+\alpha)^2 (M-\beta)}{E\rho (\alpha+\beta)^2} \quad (5)$$

Therefore, for $M \gg \alpha$, $M \gg \beta$ the maximum number of bases that can be interrogated for a fixed migration distance L is:

$$M_{max} \approx \left[ \left( \frac{\rho V (\alpha+\beta)^2}{Sk_B T} \right) \right]^{1/3} \quad (6)$$

where V=E L.

Equation (4) is similar to equation (3) derived by Mayer et al., Anal. Chem., 66(10), 1777–1780, 1994, except for a small numerical factor close to unity. Based upon these calculations and using standard optical diffraction limited measurement schemes, it is suggested that, in the case of DNA sequencing, nearly 3000 bases can be separated in 5 minutes with an initial dispersion bandwidth of 1 micron under 100 kV.

According to the present invention, by applying a voltage close to the dielectric breakthrough of the solution, for example, as $10^4$–$10^5$ V/cm, and enhancing the detection limit, the theoretical separation performance can be improved. For example, with a field strength 10 times stronger, the separation length decreases by 10 times as well as the diffusion spread down to 0.1 micron, whilst the duration of separation decreases by a factor 100. Accordingly, the investigators of this invention have demonstrated near-field measurements with spatial resolution of 0.8 nm, thus permitting achieving sequencing speeds that are at least 100 times faster and capable of sequencing longer molecular lengths than far field detection.

VIII. The Invention In a Gel Embodiment

Figure 10:
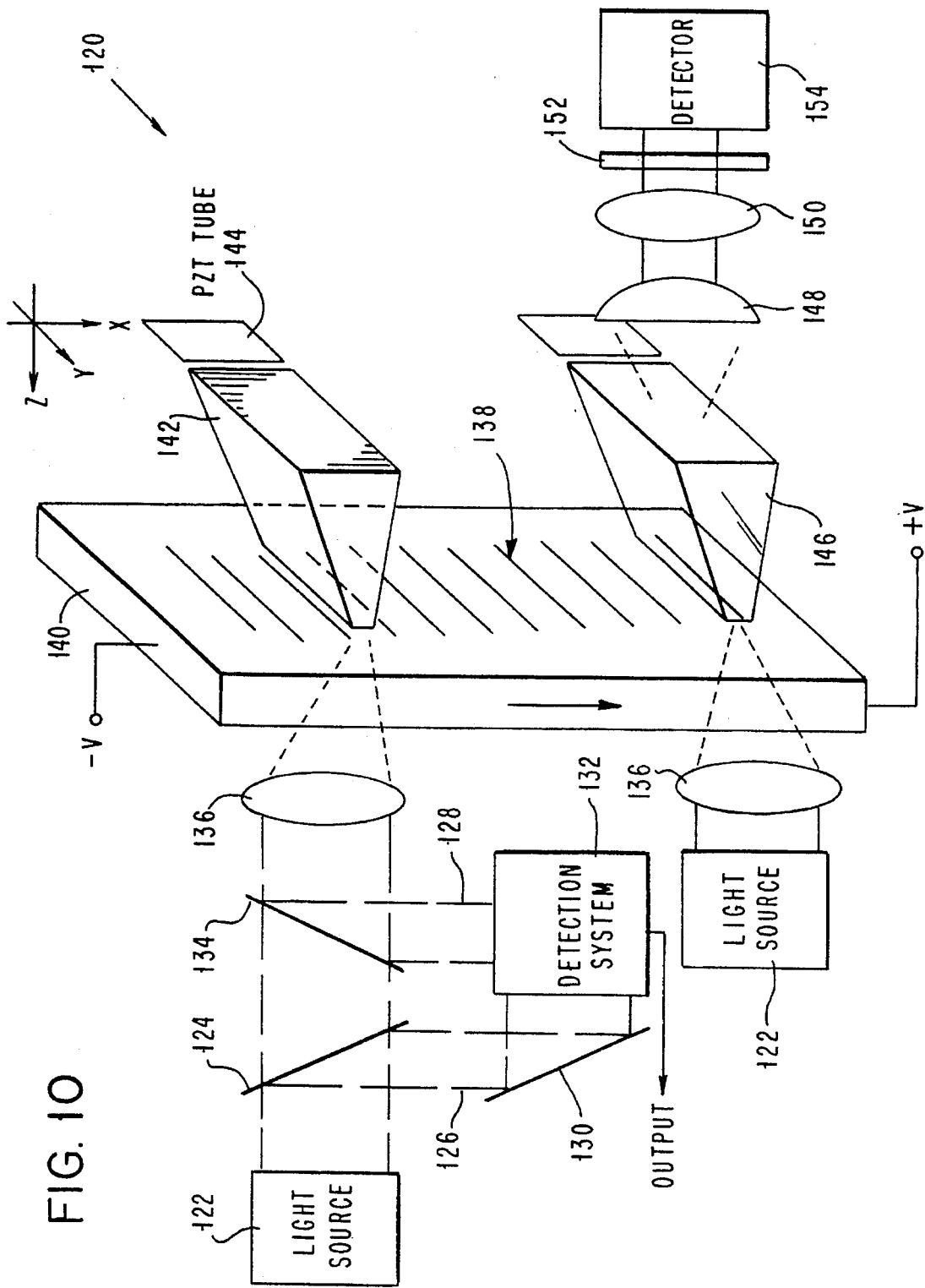
FIG. 10 shows an assembly employed to realize the invention in a gel embodiment.

Attention is now directed to FIG. 10, which shows an assembly 120 that may be used to realize the invention in a gel embodiment.

The FIG. 10 assembly 120 includes a light source 122, preferably comprising a laser coherent beam operating at fixed or tunable frequency in CW mode or pulsed mode in the x-ray, UV, visible, IR or microwave part of the spectrum. The light source 122 can transmit an excitation radiation to a beam splitter 124, thereby dividing the beam into reference 126 and signal 128 beams.

The reference beam 126 can be reflected on a mirror 130 and then directed to an interferometric detection system 132. The signal beam may be serially transmitted through a beam splitter 134, and an optical element 136 (preferably with refractive index matching liquid and preferably comprising a liquid immersion lens), for focusing the signal beam at an optical diffraction limit spot size on the surface of a band 138 of a gel 140 illuminating a sample. The illumination of a band comprising a sample is preferably at an angle above the critical angle, thereby providing an evanescent field.

The sample is preferably loaded in a slab gel or a gel tube (glass or quartz tubing ranging from 1 mm to a few microns internal diameter; typically an 8% polyacrylamide/6M urea gel) connecting two containers of standard electrophoresis buffer kit (Biorad, Pharmacia Biotech). The sample can be made to migrate through the gel 140 with the aid of a power source, thereby creating a steady or a pulsed electric field.

The incident signal beam 128 can impinge an end of an apertureless near-field probe 142. The near-field probe 142 preferably has small dimensions, on the order of atomic dimensions, and therefore preferably comprises a sharp metallic tip or an uncoated silicon tip or a tip coated with a conductive layer, thereby improving confinement of the electromagnetic field.

Employing a mechanical or piezoelectric means 144 e.g., a piezoelectric tube, the probe 142 can be moved in the x and y directions above the sample band 138 for positioning a specific region of the band of the gel. The piezoelectric tube can be used to dither the probe 142 in the z direction (for example, with a vibration amplitude of about 1–100 nm at 100–300 kHz).

The signal beam is forward scattered by the tip and reflected back through the sample into the same collimating lens 136, then transmitted through the beam splitter 134 to the interferometric detection system 132. The detection system 132 is capable of measuring the phase or amplitude of the optical beams, for example, by means of an optical differential Nomarski or any other interferometer, thereby providing an output signal representative of the sample optical properties with atomic or sub-nanometer spatial resolution.

FIG. 10 also shows an assembly utilizing an apertured near-field probe 146 preferably comprising a tapered glass probe. The construction and dimensioning of such tapered glass probes are well known in the art, and are described, for example, in U.S. Pat. No. 5,272,330, Dec. 21, 1993, incorporated by reference herein. FIG. 10 shows that light from the light source 122 may be focused onto the sample band 138 by means of the optical element 136 which preferably comprises a liquid immersion lens. The reflected or emitted light may be collected by the apertured near-field probe 146 and directed via a cylindrical lens 148, an objective lens 150, and filters 152 to a detector 154. The detector 154 preferably comprises a photomultiplier or avalanche photon diode counter.

The present invention illustrates several embodiments in a so-called collection-transmission mode, but alternatively, a collection-reflection mode is also readily realized mutatis mutandis. See, for example, U.S. Pat. Nos. 4,947,034, Aug. 7, 1990 and 4,917,462, Apr. 17, 1990.

The sample preparation for the method of the present embodiment of this invention may be conducted by reference to the known art, for example, using the procedures described by the manufacturers of sequencers (Applied Biosystems, Pharmacia Biotech). Typically, proteins can be prepared by Edman's derivatization in N-terminal or C-terminal sequencing method using alternative derivatizing reagents commercially available from e.g., Hewlett-Packard., whilst nucleic acids such as DNA can be prepared by chemical method (Maxam and Guilbert) or enzymatic method (Sanger), prior to electrophoresis, as described in "Molecular Cloning: A laboratory Manual", Sambrook, Maniatis, Coulsen, Cold Spring Harbor Laboratory, 1989. In the case of DNA, amplification reactions of DNA segments can also be performed by the polymerase chain reaction (PCR) using published methods. An electrophoretic gel may be prepared from polyacrylamide or its equivalent gel, at various concentrations ranging from an ultra-thin gel up to a slab gel. The fragments of a sample or like may be conventionally loaded into the gel wells (4 lanes corresponding to the 4 bases). The fluorescent dye-labeling of oligonucleotides used in automated techniques is also practicable.

IX Preferred Assemblies

We now disclose a system, which may be microfabricated, that can provide high speed separations while permitting one to run a full sequence of an original biomolecule that can be used for high-throughput DNA sequencing. We describe a technique of free-solution electrophoresis coupled with a physical process, leading to an accurate initial positioning of a sample followed by near-field scanning probe microscopy detection. The detection scheme can provide high accuracies in collecting the data points required to make a base call (see Section VI, supra) and in securing manipulations of a particular sequence, for example on a DNA strand as long as 3000 bases, at least 100 times faster than prior art techniques.

In accordance with the present invention, the implementation of in situ near-field spectroscopic technique under well-defined free-solution flow can provide a means of improving critical operating parameters in electrophoretic processes, in particular in gel matrices such as agarose gels in DNA sequencing. At high field strengths, molecular mobilities μ do not vary logarithmically with molecular size M due to complex molecular distortions by the field. In free-solution, the oligomeric behavior is observed to be in an oriented and stretched coiled configuration, resulting in approximately linear dependence of mobilities, defined as the velocity v per unit field E, on field strength. In the case of nucleic acids, larger molecular size can linearly lead to a higher charge density., thereby resulting in constant charge/friction ratios, and thereby generating size-independent mobilities preventing separation.

According to this invention, the modification of the charge to friction ratio by attaching high-friction coefficient species coupled with simultaneous axialized magnetic field excitation can produce size- dependent free-solution migration, assuming no significant hydrodynamic or field heterogeneities. Various aspects of the mathematical formalism of this invention, as well as the estimation of the performance of the method, have been described in Section VII, supra. Here, we describe basic experimental configurations that can be used to sequence 3000 bases in 3 seconds, if one takes a container typically 10 cm long, whilst keeping an applied voltage of 100 kV, initially defining and detecting; band widths with an accuracy below 0.1 microns.

FIG. 11 shows a system 156 suitable for this purpose. The system 156 comprises a light source 158, preferably including a metal-coated strip that can function as a small near-field probe aperture 160. The probe aperture 160 covers a container 162 comprising a fluid channel 164, having an inlet 166 and an outlet 168 and a pair of parallel electrodes 170. The electrodes 170 preferably comprise vacuum evaporated aluminum or silicon electrodes. Note that higher throughput may be obtained by employing n probes per channel or n probes per n channels. A light detector 172 may be combined with this arrangement, as shown, in order to detect the light emitted from an illuminated biomolecular sample 174.

Electrodes and insulating glass or silicon oxide surfaces inside the channel 164 preferably are surface treated, for example, with fluorosilane, to prevent nonspecific macromolecular adhesion. This method can introduce covalently linked carboxyl groups on the silicon oxide surface, thereby increasing negative charge density and thereby preventing DNA anchorage.

The sample solution can be introduced from the inlet 166 and dragged or pumped to the fluid channel 164 that can handle up to large DNA's of several hundreds kilobases. At the same time, the electrodes may be energized for aligning the biomolecular sample 174 onto one electrode surface 170.

The biomolecular sample 174 preferably is end-labeled with a magnetic molecule such as ferritin or a magnetic bead bound to a large monodisperse labelling protein, or chemicals like streptavidin, and can be elongated with an end fixed at an electrode when an electromagnetic field B is applied. Note that the free-solution electrophoresis must be performed in a specific medium satisfying the hydrodynamic drag and the electrostatic requirements, such as the electrode configurations and the electric field conditions. (See Section VII, supra.)

At first, a strong magnetic field gradient B and a weak electric field E can induce an alignment of the molecules at one electrode 170. Then, a high voltage, typically generated by a 100 kV power supply 176 may be applied to the electrode 170 so that the field drags the flowing biomolecules 174 towards the other uncovered electrode 170.

Since biomolecules 174, and in particular DNA stretched by an electric field E, can shrink back to random-coil conformation, a constant magnetic excitation B preferably is kept, thereby retaining the stretched molecular conformation when the electric field E is turned up ($E > 10^6$ V/M).

The strength of the magnetic field B may be generated by using one electromagnetic device 178, for example, producing up to 2 Telsa, with the proviso that the net magnetic force is strong enough to pull the biomolecule against the electrodes 170 and overcome the Brownian motion.

Biomolecules 174 migrate toward a detection region where qualitative and quantitative near-field measurements may be made by measuring either the fluorescent intensity of dye-labels along a biomolecular length, using for example a photomultiplier, or the absorption properties of readable bases, using an optical spectrometer.

The spatial resolution provided by this physical process, leading to biomolecular manipulation coupled with the advantage of near-field measurement and free-solution separation, enables the location of each migrating biomolecule or fragment within a spatial resolution below the diffraction limit, so that the reconstruction of a total code sequence can become accurate and fast.

An application of such a device FIG. 11 system 156 may be found in a detection of DNA probe/target hybridization technique. Here, a DNA sample may be denatured, i.e., separated into two single-strands, and deposited on an array of immobilized single-stranded nucleic acids fragments in the fluid channel 164 of the previously described microfabricated silicon oxide surface. Formation of a hybrid among a tagged sample with DNA probes of a known sequence can indicate that the target sequence complementary to the respective anchored probes exist in the sample. A detection of optically readable tags (succinylfluorescein derivatives or other commercially available chemicals) can be achieved by using a near-field optical technique.

The above anchorage event may require a simultaneous electrostatic interaction by using an additional electrode configuration (i.e., perpendicular to sample migration), regardless of how nucleic acids probes may be fixed, as well as an addition of divalent positive ions, such as calcium or magnesium ions, in fixing the fragments onto the glass or (quartz) fluid channel 164. The ions can act as an adhesive between the negatively charged DNA and the negatively charged substrate. It is also possible to obtain a similar surface treatment by plasma discharge in an appropriate environment (for example, amylamine and derivatives).

The FIG. 11 system 156 preferably comprises an integrated device. Our attention is now directed to FIGS. 12 and 13, which show illustrative assemblies that may be employed for providing an accurate readout of base sequences interrogated by the FIG. 11 system 156.

FIG. 12 shows an assembly 180 suitable for readout for a case where a near-field detector comprises an aperatured probe 182. In particular, the FIG. 12 assembly 180 includes a near-field probe 182 comprising a small microlithographic window, through which a light signal may be transmitted to a sample 184 and collected by a detector 186.

The geometry of the near-field probe 182 window preferably is chosen based on the following considerations: (1) a width (x) of the window parallel to a migrating fluid flow direction is made small enough, typically about 20 nm in thickness, thereby restricting a sample in the near-field for better resolution, whilst (ii) a perpendicular width (y) may be somewhat larger to accept fluorescence measurement over a certain number of molecules (184) when they are scanned with a laser beam and the emission collected through a high N.A. (numerical aperture) liquid immersion objective 188. A thin aluminum layer of approximately the thickness of three penetration skin depths (30 nm) can be used as an opaque screen material.

As the near-field probe 182 response function is dependent on the sample to probe spacing, the thin transmissive silicon membrane at the bottom of the light source element has to be made in approximately the same size as the aperture size for better resolution.

A laser light source 190 can be coupled into the near-field probe 182, with an optical fiber 192 preferably acting as either an excitation or collection optical element that can be adjusted close to the sample or even scanned by using standard piezoelectric tubes 194.

The process for data acquisition may be accomplished by recording the optical intensity collected From the high N.A. liquid immersion lens 188. The light is then preferably sent through a combination of a mirror 196 and a series of notch filters 198 for discriminating the emission light from the residual laser excitation light. The light is subsequently detected, preferably by way of the detector 186 which preferably comprises a photomultiplier or a high quantum efficiency low noise photodiode. (See U.S. Pat. No. 5,272, 330, incorporated by reference herein.)

As the near-field probe 182 is preferably vertically modulated (about 10 nm p-p), the near-field signal is sent to a lock-in amplifier 200 in order to demodulate a resultant AC signal. An independent feedback loop 202 can also be used to control probe-sample spacing via an acoustic optical modulator (AOM) and a controller 204.

Note that in accordance with this embodiment, the light path can be reversed from a transmission mode to a collection mode—but the sensitivity of the near-field measurement in the collection mode may be weaker. The collection mode can be realized by using similar conjugated optical elements (188',—196',—198',—186') as shown in FIG. 12.

Attention is now directed to FIG. 13 which shows an assembly 206 suitable for readout for a case where a near-field probe comprises an apertureless probe 208.

The apertureless probe 208 preferably comprises a microfabricated strip 210, on a sub-10 nm scale, preferably placed on the top of a thin supporting membrane 212. The membrane 212 may be set into vibration at a frequency preferably near its resonance (for example, 100–300 kHz, spring constant in the 10–50 N/m) by the action preferably of a piezo-electric ceramic element 214, thereby producing a movement parallel to an electrophoretic flow induced by applied electromagnetic fields.

An illuminating laser source 216 preferably outputs polarized light that preferably is passed through a Nomarski liquid immersion objective 218 (or a Wollaston prism) via an isolator 220 (which can rotate the polarization by 45 degrees), an expander 222, and a beamsplitter 224. The light is then preferably split into two orthogonally polarized beams resulting in two spots brought across the fluid channel into two loci on the micro- fabricated strip 210.

The reflected light from the two spots returns via the beamsplitter 224 onto an analyzer 226, comprising a Wollaston prism positioned with its axis at 45 degrees with respect to the Nomarski prism 218. The reflected beams are thereby preferably recombined by way of a differential photodiode arrangement 228 for detecting an output signal proportional to the phase difference imparted to the scattered field from the tip. During the electrophoresis, as the biomolecular sample migrates relative to the near-field probe 208, variations of the electric field of the tip are modulated by the sample properties, and they are recorded sequentially through an electronics comprising a lock-in amplifier 230 and a controller 232, and then by way of a computer 234. The computer 234 can correlate the raw data from the band and determine the code sequence of the biomolecule in a manner described above in Section VI.

We claim:

1. A method suitable for identifying a code sequence of at least a portion of a biomolecule, the method comprising the steps of:

1) using a near-field probe technique for generating a super-resolution chemical analysis of the portion of a biomolecule below the diffraction limit of one half the wavelength of the probing radiation;

and 2) correlating the chemical analysis with a broad spectral content of a referent biomolecule for generating a code sequencing of the portion of the biomolecule.

2. A method according to claim 1, comprising a step of generating a code sequence for a portion of a biomolecule comprising DNA.

3. A method according to claim 1, comprising a step of generating a code sequence for a portion of a biomolecule comprising RNA.

4. A method according to claim 1, comprising a step of generating a code sequence for a portion of a biomolecule comprising a protein.

5. A method according to claim 1, comprising a step of generating a code sequence for a carbohydrate.

6. A method according to claim 1, wherein a portion of a biomolecule comprises purines and pyrimidines bases.

7. A method according to claim 1, comprising generating a code sequence for a portion of a biomolecule comprising a nucleic acid having at least 1000 bases/portion.

8. A method according to claim 7 comprising generating a code sequence that is endomorphic with the bases.

9. A method according to claim 7, comprising generating within less than 1 hour a code sequence comprising at least 1000 bases/portion.

10. A method according to claim 9, comprising generating within less than 1 hour a code sequence comprising at least 100'000 bases/portion.

11. A method according to claim 1, comprising generating a code sequence for a portion of a biomolecule comprising a carbohydrate having at least 1000 residue per portion.

12. A method according to claim 1, comprising a step of interrogating a portion of a biomolecule at a resolution below the optical diffraction limit.

13. A method according to claim 1, comprising a step of interrogating a portion of a biomolecule from a sub-nanometer resolution up to the diffraction limit.

14. A method according to claim 1, comprising a step of interrogating a portion of a biomolecule by near-field acoustic microscopy.

15. A method according to claim 1, comprising a step of interrogating a portion of a biomolecule by magnetic force microscopy.

16. A method according to claim 1, comprising a step of interrogating a portion of a biomolecule by near-field optical microscopy.

17. A method according to claim 1, comprising a step of interrogating a portion of a biomolecule by near-field thermal probe microscopy.

18. A method according to claim 1, wherein the super-resolution chemical analysis comprises absorption spectroscopic information.

19. A method according to claim 1, wherein the super-resolution chemical analysis comprises identifying magnetic properties of the portion of the biomolecule.

20. A method according to claim 1, wherein the super-resolution chemical analysis comprises identifying thermal properties of the portion of the biomolecule.

21. A method according to claim 1, wherein the super-resolution chemical analysis comprises emission spectroscopic information.

22. A method according to claim 1, comprising separating a portion of a biomolecule by a sequencing reaction into independent sub-units uniquely identifiable by predetermined magnetic properties.

23. A method according to claim 1, comprising separating a portion of a biomolecule by using gel-electrophoresis.

24. A method according to claim 1, comprising generating a fast code sequencing comprising identifying at least 200 building blocks per hour.

25. A method according to claim 1, comprising a step of deriving the broad spectral content of the referent biomolecule from a portion of the biomolecule itself.

26. A method according to claim 1, comprising a step of deriving the broad spectral content of the referent biomolecule from a second independent biomolecule.

27. A method according to claim 1, comprising generating a code sequence for a portion of a biomolecule comprising a protein having at least 1000 amino acids per portion.

28. A method according to claim 2, comprising generating within less than 1 hour a code sequence for a portion of a biomolecule comprising a protein having at least 1000 amino acids per portion.

29. A method according to claim 1, comprising a step of separating a portion of a biomolecule by a sequencing reaction into independent sub-units uniquely identifiable by predetermined absorbant labels.

30. A method according to claim 29, wherein a label is fluorescent.

31. A method according to claim 1, comprising separating a portion of a biomolecule by using free-solution electrophoresis.

32. A method according to claim 31, comprising initial stretch-and- positioning of a portion of a biomolecule at a surface.

33. A method according to claim 32, comprising initial magnetic stretch-and-positioning of a portion of a biomolecule at an electrode surface.

34. A method according to claim 32, comprising initial electrostatic stretch-and-positioning of a portion of a biomolecule at an electrode surface.

35. A method according to claim 32, comprising initial electrostatic and magnetic stretch and positioning of a portion of a biomolecule at an electrode surface.

36. A method according to claim 32, comprising initial electromagnetic stretch-and-positioning of a portion of a biomolecule by optical forces at an electrode surface.

37. A method according to claim 36, comprising initial stretch-and-positioning of a portion of a biomolecule by viscous drag.

38. A method according to claim 32, comprising anchoring a portion of a biomolecule at a solid matrix.

39. A method according to claim 38, comprising end-labeling a portion of a biomolecule with large monodisperse labeling proteins or chemicals.

40. A method suitable for identifying a code sequence of at least a portion of a biomolecule, the method comprising the steps of:

1) using a super resolution apertureless near-field scanning probe for interrogating absorption properties characteristic of a portion of the biomolecule;
and
2) correlating the characteristic with a spectral content of a referent absorbant, for generating a code sequencing of the portion of the biomolecule.

41. A method suitable for identifying a code sequence of at least a portion of an arbitrary biomolecule, the method comprising the steps of:

1) generating a broad spectral content information base for a referent biomolecule;
2) using a near-field scanning probe technique for generating a super-resolution chemical analysis of a portion of the arbitrary biomolecule;
and
3) correlating the super-resolution chemical analysis for the arbitrary biomolecule with the broad spectral content information base of the referent biomolecule, for generating a code sequencing of the portion of the arbitrary biomolecule.

42. A method according to claim 41, wherein step (1) comprises generating a broad spectral content information base for a referent biomolecule by using a far-field detector probe.

43. A method according to claim 41, comprising:

1) using a near-field scanning probe for generating an absorption information base for a referent biomolecule;
2) using a near-field scanning probe for generating a super-resolution chemical analysis comprising a thermal information base for the portion of the arbitrary biomolecule;
and
3) correlating the absorption information base and the thermal information base as a measure of a code sequencing of the portion of the arbitrary biomolecule.

* * * * *